US007795381B2

(12) United States Patent
Celis

(10) Patent No.: US 7,795,381 B2
(45) Date of Patent: Sep. 14, 2010

(54) METHODS AND MATERIALS FOR CANCER TREATMENT

(75) Inventor: Esteban Celis, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 310 days.

(21) Appl. No.: 12/018,022

(22) Filed: Jan. 22, 2008

(65) Prior Publication Data

US 2008/0119636 A1    May 22, 2008

Related U.S. Application Data

(62) Division of application No. 10/474,521, filed as application No. PCT/US02/10583 on Apr. 5, 2002, now abandoned.

(60) Provisional application No. 60/282,633, filed on Apr. 9, 2001.

(51) Int. Cl.
*C07K 5/00* (2006.01)
*C12N 15/00* (2006.01)

(52) U.S. Cl. .................. 530/300; 530/326; 530/327; 530/328; 435/69.2

(58) Field of Classification Search ................... None
See application file for complete search history.

(56) References Cited

U.S. PATENT DOCUMENTS

| | | | |
|---|---|---|---|
| 4,235,871 | A | 11/1980 | Papahadjopoulos et al. |
| 4,237,224 | A | 12/1980 | Cohen et al. |
| 4,273,875 | A | 6/1981 | Manis |
| 4,363,877 | A | 12/1982 | Goodman et al. |
| 4,428,941 | A | 1/1984 | Galibert et al. |
| 4,431,739 | A | 2/1984 | Riggs |
| 4,501,728 | A | 2/1985 | Geho et al. |
| 4,837,028 | A | 6/1989 | Allen |
| 5,019,369 | A | 5/1991 | Presant et al. |
| 5,844,075 | A | 12/1998 | Kawakami et al. |
| 6,500,919 | B1 | 12/2002 | Adema et al. |

FOREIGN PATENT DOCUMENTS

| | | |
|---|---|---|
| WO | WO 94/03205 | 2/1994 |
| WO | WO 95/19783 | 7/1995 |
| WO | WO 95/22317 | 8/1995 |
| WO | WO 95/29193 | 11/1995 |
| WO | WO 97/34617 | 9/1997 |
| WO | WO 98/33888 | 8/1998 |
| WO | WO 99/45954 | 9/1999 |
| WO | WO 01/90197 | 11/2001 |

OTHER PUBLICATIONS

Tsai et al J Immuno vol. 158, p. 1796-1802, 1997.*
GenBank Accession No. M32295 dated Apr. 27, 1993.
GenBank Accession No. M77348 dated Jan. 8, 1995.

Abbas et al., "Binding of Peptides to Major Histocompatibility Complex Molecules," *Cellular and Molecular Immunology*, 2000, 4th Edition, pp. 71-72.
Boon and van der Bruggen, "Human Tumor Antigens Recognized by T Lymphocytes," *J. Exp. Med.*, 1996, 183:725-729.
Bruce, "Evaluation of Functional Capacity and Exercise Tolerance of Cardiac Patients," *Mod. Concepts Cardiovasc.*, 1956, 25:321-326.
Castelli et al., "Novel HLA-Cw8-Restricted T Cell Epitopes Derived from Tyrosinase-Related Protein-2 and gp100 Melanoma Antigens," *J. Immunol.*, 1999, 162:1739-1748.
Chaux et al., "Identification of MAGE-3 Epitopes Presented by HLA-DR Molecules to CD4+ T Lymphocytes," *J. Exp. Med.*, 1999, 189:767-777.
Cox et al., "Identification of a Peptide Recognized by Five Melanoma-Specific Human Cytotoxic T Cell Lines," *Science*, 1994, 264:716-719.
Fritsch et al., "Immunohistologic Responses Within Dermal Metastatic Melanoma Lesions of Patients Treated With a Synthetic Peptide Vaccine," *Journal of Immunotherapy*, 2000, 23(5):557-569.
Fujita et al., "Evidence that HLA class II-restricted human CD4+ T cells specific to p53 self peptides respond to p53 proteins of both wild and mutant forms," *Eur. J. Immunol.*, 1998, 28:305-316.
Jäger et al., "Granulocyte-macrophage-colony-stimulating factor enhances immune responses to melanoma-associated peptides in vivo," *Int. J. Cancer*, 1996, 67:54-62.
Jäger et al., "Identification of NY-ESO-1 Epitopes Presented by Human Histocompatibility Antigen(HLA)-DRB4*0101-0103 and Recognized by CD4+ T Lymphocytes of Patients with NY-ESO-1-expressing Melanoma," *J. Exp. Med.*, 2000, 191:625-630.
Kawakami et al., "Identification of New Melanoma Epitopes on Melanosomal Proteins Recognized by Tumor Infiltrating T Lymphocytes Restricted by HLA-A1, -A2, and -A3 Alleles," *J. Immunol.*, 1998, 161:6985-6992.
Kawakami et al., "Recognition of Multiple Epitopes in the Human Melanoma Antigen gp100 by Tumor-Infiltrating T Lymphocytes Associated with In Vivo Tumor Regression," *J. Immunol.*, 1995, 154:3961-3968.
Kawashima et al., "Identification of GP100-derived, Melanoma-specific Cytotoxic T-Lymphocyte epitopes restricted by HLA-A3 Supertype Molecules by Primary In Vitro Immunization with Peptide-Pulsed Dendritic Cells," *Int. J. Cancer*, 1998, 78:518-524.
Kobayashi et al., "Defining Promiscuous MHC Class II Helper T-Cell Epitopes for the HER2/neu Tumor Antigen," *Cancer Res.*, 2000, 60:5228-5236.
Kobayashi et al., "MHC-Binding Peptides as Immunotherapeutics for Cancer," *Immunological Investigations*, 2000, 29(2):105-110.
Li et al., "Tumour-specific MHC-class-II-restricted responses after in vitro sensitization to synthetic peptides corresponding to gp100 and Annexin II eluted from melanoma cells," *Cancer Immunol. Immunother.*, 1998, 47:32-38.

(Continued)

*Primary Examiner*—Larry R. Helms
*Assistant Examiner*—Lei Yao
(74) *Attorney, Agent, or Firm*—Fish & Richardson P.C.

(57) ABSTRACT

Methods and materials for inducing anti-tumor responses in melanoma patients are disclosed. These methods and materials involve gp100-derived polypeptides that contain both a helper T-cell epitope and a cytotoxic T-cell epitope.

4 Claims, 7 Drawing Sheets

OTHER PUBLICATIONS

Manici et al., "Melanoma Cells Present a MAGE-3 Epitope to CD4+ Cytotoxic T Cells in Association with Histocompatability Leukocyte Antigen DR11," *J. Exp. Med.*, 1999, 189:871-876.

Marchand et al., "Tumor regression responses in melanoma patients treated with a peptide encoded by gene MAGE-3," *Int. J. Cancer*, 1995, 63:883-885.

Matteucci et al., "Synthesis of Deoxyoligonucleotides on a Polymer Support," *J. Am. Chem. Soc.*, 1981, 103:3185-3191.

Matzinger, "The JAM test. A simple assay for DNA fragmentation and cell death," *J. Immunol. Methods*, 1991, 145:185-192.

Merrifield, *The Polypeptides. Analysis, Synthesis, Biology*, Gross and Meienhofer (eds.), Academic Press, New York, 1979, pp. 1-284.

Pardoll and Topalian, "The role of CD4+ T cell responses in antitumor immunity," *Curr. Opin. Immunol.*, 1998, 10:588-594.

Reynolds et al., "HLA-Independent Heterogeneity of CD8+ T Cell Responses to MAGE-3, Melan-A/MART-1, gp100, Tyrosinase, MC1R, and TRP-2 in Vaccine-Treated Melanoma Patients," *J. Immunol.*, 1998, 161:6970-6976.

Reynolds et al., "Identification of HLA-A*03, A*11, and B*07-restricted melanoma-associated peptides that are immunogenic in vivo by vaccine-induced immune response (VIIR) analysis," *J. Immunol. Meth.*, 2000, 244:59-67.

Robbins et al., "The Intronic Region of an Incompletely Spliced gp100 Gene Transcript Encodes an Epitope Recognized by Melanoma-Reactive Tumor-Infiltrating Lymphocytes," *J. Immunol.*, 1997, 159:303-308.

Rosenberg et al., "Immunologic and therapeutic evaluation of a synthetic peptide vaccine for the treatment of patients with metastatic melanoma," *Nat. Med.*, 1998, 4:321-327.

Salazar-Onfray et al., "Synthetic Peptides Derived from the Melanocyte-stimulating Hormone Receptor MC1R Can Stimulate HLA-A2-restricted Cytotoxic T Lymphocytes That Recognize Naturally Processed Peptides on Human Melanoma Cells," *Cancer Research*, 1997, 57:4348-4355.

Skipper et al., "Shared Epitopes for HLA-A3-Restricted Melanoma-Reactive Human CTL Include a Naturally Processed Epitope from Pmel-17/gp100," *J. Immunol.*, 1996, 157:5027-5033.

Southwood et al., "Several Common HLA-DR Types Share Largely Overlapping Peptide Binding Repertoires," *J. Immunol.*, 1998, 160:3363-3373.

Surman et al., "Cutting Edge: CD4+ T Cell Control of CD8+ T Cell Reactivity to a Model Tumor Antigen," *J. Immunol.*, 2000, 164:562-565.

Szoka, Jr. et al., "Comparative Properties and Methods of Preparation of Lipid Vesicles (Liposomes)," *Ann. Rev. Biophys. Bioeng.*, 1980, 9:467-508.

Tam et al., "SN2 Deprotection of Synthetic Peptides with Low Concentration of HF in Dimethyl Sulfide: Evidence and Application in Peptide Synthesis," *J. Am. Chem. Soc.*, 1983, 105:6442-6455.

Toes et al., "CD4 T Cells and Their Role in Antitumor Immune Responses," *J. Exp. Med.*, 1999, 189:753-756.

Touloukian et al., "Identification of a MHC Class II-Restricted Human gp100 Epitope Using DR4-IE Transgenic Mice," *J. Immunol.*, 2000, 164:3535-3542.

Tsai et al., "Identification of Subdominant CTL Epitopes of the GP100 Melanoma-Associated Tumor Antigen by Primary In Vitro Immunization with Peptide-Pulsed Dendritic Cells," *J. Immunol.*, 1997, 158:1796-1802.

Wang and Rosenberg, "Human tumor antigens for cancer vaccine development," *Immunol. Rev.*, 1999, 170:85-100.

Weber et al., "A Phase I Trial of an HLA-A1 Restricted MAGE~3 Epitope Peptide with Incomplete Freund's Adjuvant in Patients with Resected High-Risk Melanoma," *J. Immunother.*, 1999, 22:431-440.

Yasukawa et al., "CD4+ Cytotoxic T-Cell Clones Specific for bcr-abl b3a2 Fusion Peptide Augment Colony Formation by Chronic Myelogenous Leukemia Cells in a b3a2-Specific and HLA-DR-Restricted Manner," *Blood*, 1998, 92:3355-3361.

Zaks and Rosenberg, "Immunization with a Peptide Epitope (p. 369-377) from HER-2/neu Leads to Peptide-specific Cytotoxic T Lymphocytes That Fail to Recognize HER-2/neu+ Tumors," *Cancer Res.*, 1998, 58:4902-4908.

Zarour et al., "Melan-A/MART-151-73 represents an immunogenic HLA-DR4-restricted epitope recognized by melanoma-reactive CD4+ T cells," *Proc. Natl. Acad. Sci. USA*, 2000, 97:400-405.

Zarour et al., "NY-ESO-1 Rncodes DRB1*0401-restricted Epitopes Recognized by Melanoma-reactive CD4+ T Cells," *Cancer Res.*, 2000, 60:4946-4952.

Zeng et al., "Identification of CD4+ T Cell Epitopes from NY-ESO-1 Presented by HLA-DR Molecules," *J. Immunol.*, 2000, 165:1153-1159.

* cited by examiner

Figure 7. Peptides predicted to be promiscuous HTL epitopes.

| Sequence (9-mer core) | Posit. of 1st core residue | DR1 ARB[a] | DR1 rank | DR4 ARB | DR4 rank | DR7 ARB | DR7 rank | Rank sum[b] | HTL peptide name | Peptide sequence[c] | Adjoining CTL epitope(s) |
|---|---|---|---|---|---|---|---|---|---|---|---|
| MSTPEATGM | 392 | 399.6 | 5 | 44.61 | 4 | 270.8 | 1 | 10 | gp100$_{389-403}$ | LAEMSTPEATGMTPA | |
| ISTAPVQMP | 359 | 36.35 | 25 | 64.82 | 2 | 250.4 | 14 | 29 | gp100$_{356-370}$ | TEVISTAPVQMPTAE | |
| VSTQLIMPG | 580 | 85.89 | 15 | 83.21 | 1 | 22.86 | 14 | 30 | gp100$_{576-590}$ | SLAV_VSTQLIMPG_QE* | [gp100$_{570-579}$][d] |
| LVLMAVVLA | 604 | 948.1 | 2 | 23.68 | 10 | 14.81 | 21 | 33 | gp100$_{601-615}$ | GILL_VLMAVVLA_SLI* | [gp100$_{614-622}$][e] [gp100$_{619-627}$][f] |
| MPTAESTGM | 366 | 46.13 | 23 | 30.01 | 8 | 94.11 | 4 | 35 | gp100$_{366-380}$ | PVQMPTAESTGMTPE | |
| MLGTHTMEV | 178 | 154.1 | 9 | 7.31 | 25 | 56.88 | 5 | 39 | gp100$_{175-189}$ | GRA _MLGTHTMEV_TVY* | [gp100$_{177-186}$][d] |
| LIGANASFS | 77 | 89.32 | 13 | 4.42 | 31 | 37.44 | 9 | 53 | gp100$_{74-89}$ | GPT_LIGANASFS_IALN* | [gp100$_{70-78}$][g] [gp100$_{87-95}$][h] |
| LQAAIPLTS | 292 | 57.34 | 19 | 37.36 | 27 | 41.27 | 8 | 54 | gp100$_{289-304}$ | QVV_LQAAIPLTS_CGS* | |
| VTAQVVLQA | 286 | 721.3 | 4 | 3.42 | 34 | 20.65 | 16 | 54 | gp100$_{283-297}$ | PGPVTAQVVLQAAIP | [gp100$_{280-288}$][i] |
| LRNQPLTFA | 233 | 92.18 | 14 | 26.86 | 9 | 5.07 | 35 | 58 | gp100$_{230-244}$ | KHF_LRNQPLTFA_LQL | |

[a] Average Relative Binding, as defined in the text.
[b] Rank sum = DR1 rank + DR4 rank + DR7 rank.
[c] Peptide sequences in italics were selected for synthesis for T-cell studies. Peptides marked with an "*" are situated near a known CTL epitope. Underlined residues correspond to the 9-mer core sequence.
[d] Subdominant CTL epitopes restricted by HLA-A2 identified by Tsai, et al, J Immunol 158:1796 1997.
[e] CTL epitope restricted by HLA-A3 identified by Kawakami, et al, J Immunol 161:6985 (1998).
[f] CTL epitope restricted by HLA-A2 identified by Kawakami, et al, J Immunol 161:6985 (1998).
[g] CTL epitope restricted by HLA-Cw8 identified by Castelli, et al, J Immunol 162:1739 (1999).
[h] CTL epitope restricted by HLA-A3 and -A11 identified by Kawashima et al, Int J Cancer 78:518 (1998).
[i] CTL epitope restricted by HLA-A2 identified by Kawakami, et al, J Immunol 154:3961 (1995) and by Cox, et al, Science 264:716 (1994).

```
SEQUENCE LISTING

<160> NUMBER OF SEQ ID NOS: 20

<210> SEQ ID NO 1
<211> LENGTH: 15
<212> TYPE: PRT
<213> ORGANISM: Homo sapiens

<400> SEQUENCE: 1

Leu Ala Glu Met Ser Thr Pro Glu Ala Thr Gly Met Thr Pro Ala
 1               5                  10                  15

<210> SEQ ID NO 2
<211> LENGTH: 15
<212> TYPE: PRT
<213> ORGANISM: Homo sapiens

<400> SEQUENCE: 2

Thr Glu Val Ile Ser Thr Ala Pro Val Gln Met Pro Thr Ala Glu
 1               5                  10                  15
```

```
<210> SEQ ID NO 3
<211> LENGTH: 15
<212> TYPE: PRT
<213> ORGANISM: Homo sapiens

<400> SEQUENCE: 3

Ser Leu Ala Val Val Ser Thr Gln Leu Ile Met Pro Gly Gln Glu
 1               5                  10                  15

<210> SEQ ID NO 4
<211> LENGTH: 15
<212> TYPE: PRT
<213> ORGANISM: Homo sapiens

<400> SEQUENCE: 4

Gly Ile Leu Leu Val Leu Met Ala Val Val Leu Ala Ser Leu Ile
 1               5                  10                  15

<210> SEQ ID NO 5
<211> LENGTH: 15
<212> TYPE: PRT
<213> ORGANISM: Homo sapiens

<400> SEQUENCE: 5

Pro Val Gln Met Pro Thr Ala Glu Ser Thr Gly Met Thr Pro Glu
 1               5                  10                  15

<210> SEQ ID NO 6
<211> LENGTH: 15
<212> TYPE: PRT
<213> ORGANISM: Homo sapiens

<400> SEQUENCE: 6

Gly Arg Ala Met Leu Gly Thr His Thr Met Glu Val Thr Val Tyr
 1               5                  10                  15

<210> SEQ ID NO 7
<211> LENGTH: 16
<212> TYPE: PRT
<213> ORGANISM: Homo sapiens

<400> SEQUENCE: 7

Gly Pro Thr Leu Ile Gly Ala Asn Ala Ser Phe Ser Ile Ala Leu Asn
 1               5                  10                  15

<210> SEQ ID NO 8
<211> LENGTH: 15
<212> TYPE: PRT
<213> ORGANISM: Homo sapiens

<400> SEQUENCE: 8

Gln Val Val Leu Gln Ala Ala Ile Pro Leu Thr Ser Cys Gly Ser
 1               5                  10                  15

<210> SEQ ID NO 9
<211> LENGTH: 15
<212> TYPE: PRT
<213> ORGANISM: Homo sapiens

<400> SEQUENCE: 9

Pro Gly Pro Val Thr Ala Gln Val Val Leu Gln Ala Ala Ile Pro
 1               5                  10                  15
```

```
<210> SEQ ID NO 10
<211> LENGTH: 15
<212> TYPE: PRT
<213> ORGANISM: Homo sapiens

<400> SEQUENCE: 10

Lys His Phe Leu Arg Asn Gln Pro Leu Thr Phe Ala Leu Gln Leu
 1               5                  10                  15

<210> SEQ ID NO 11
<211> LENGTH: 21
<212> TYPE: PRT
<213> ORGANISM: Homo sapiens

<400> SEQUENCE: 11

Ser Leu Ala Asp Thr Asn Ser Leu Ala Val Val Ser Thr Gln Leu Ile
 1               5                  10                  15

Met Pro Gly Gln Glu
            20

<210> SEQ ID NO 12
<211> LENGTH: 22
<212> TYPE: PRT
<213> ORGANISM: Homo sapiens

<400> SEQUENCE: 12

Gly Ile Leu Leu Val Leu Met Ala Val Val Leu Ala Ser Leu Ile Tyr
 1               5                  10                  15

Arg Arg Arg Leu Met Lys
            20

<210> SEQ ID NO 13
<211> LENGTH: 27
<212> TYPE: PRT
<213> ORGANISM: Homo sapiens

<400> SEQUENCE: 13

Gly Ile Leu Leu Val Leu Met Ala Val Val Leu Ala Ser Leu Ile Tyr
 1               5                  10                  15

Arg Arg Arg Leu Met Lys Gln Asp Phe Ser Val
            20                  25

<210> SEQ ID NO 14
<211> LENGTH: 20
<212> TYPE: PRT
<213> ORGANISM: Homo sapiens

<400> SEQUENCE: 14

Val Ser Asn Asp Gly Pro Thr Leu Ile Gly Ala Asn Ala Ser Phe Ser
 1               5                  10                  15

Ile Ala Leu Asn
            20

<210> SEQ ID NO 15
<211> LENGTH: 22
<212> TYPE: PRT
<213> ORGANISM: Homo sapiens

<400> SEQUENCE: 15

Gly Pro Thr Leu Ile Gly Ala Asn Ala Ser Phe Ser Ile Ala Leu Asn
 1               5                  10                  15

Phe Pro Gly Ser Gln Lys
            20
```

```
<210> SEQ ID NO 16
<211> LENGTH: 24
<212> TYPE: PRT
<213> ORGANISM: Homo sapiens

<400> SEQUENCE: 16

Leu Glu Pro Gly Pro Val Thr Ala Gln Val Val Leu Gln Ala Ala Ile
 1               5                  10                  15
Pro Leu Thr Ser Cys Gly Ser Ser
            20

<210> SEQ ID NO 17
<211> LENGTH: 9
<212> TYPE: PRT
<213> ORGANISM: Homo sapiens

<400> SEQUENCE: 17

Met Leu Gly Thr His Thr Met Glu Val
 1               5

<210> SEQ ID NO 18
<211> LENGTH: 9
<212> TYPE: PRT
<213> ORGANISM: Homo sapiens

<400> SEQUENCE: 18

Val Ser Asn Asp Gly Pro Thr Leu Ile
 1               5

<210> SEQ ID NO 19
<211> LENGTH: 9
<212> TYPE: PRT
<213> ORGANISM: Homo sapiens

<400> SEQUENCE: 19

Ala Leu Asn Phe Pro Gly Ser Gln Lys
 1               5

<210> SEQ ID NO 20
<211> LENGTH: 9
<212> TYPE: PRT
<213> ORGANISM: Influenza virus

<400> SEQUENCE: 20

Gly Ile Leu Gly Phe Val Phe Thr Leu
 1               5
```

METHODS AND MATERIALS FOR CANCER TREATMENT

CROSS REFERENCE TO RELATED APPLICATIONS

This application is divisional of U.S. application Ser. No. 10/474,521, filed May 12, 2004, which is a National Stage application under 35 U.S.C. §371 that claims the benefit of PCT/US02/10583, filed Apr. 5, 2002, which claims the benefit of U.S. Provisional application Ser. No. 60/282,633, filed Apr. 9, 2001.

STATEMENT AS TO FEDERALLY SPONSORED RESEARCH

This invention was made with government support under the National Institute of Health (Grants CA80782 and CA82677). The government has certain rights in the invention.

BACKGROUND

1. Technical Field

The invention relates to polypeptides. More particularly, the invention relates to gp100-derived polypeptides that contain both a helper T-cell epitope and a cytotoxic T-cell epitope.

2. Background Information

For some time many groups have been actively identifying cytotoxic T lymphocyte (CTL) epitopes for various tumor-associated antigens (TAA) and synthetic polypeptides representing these epitopes have been used to prepare therapeutic vaccines to treat cancer patients (Marchand M P et al., *Int J of Cancer* 63:883 (1995); Jager E et al., *Int J of Cancer* 67:54 (1996); Weber J et al., *J Immunother* 22:431 (1999); Rosenberg S A et al., *Nat Med* 4:321 (1998); and Zaks T Z et al., *Cancer Res* 58:4902 (1998)). However, therapeutic effects of these vaccines are far from optimal.

Several TAA are possible targets for developing T-cell immunotherapy against malignant melanoma (Boon, T et al., *J Exp Med* 183:725 (1996) and Wang R F et al., *Immunol Rev* 170:85 (1999)). Amongst these, the melanocyte-related antigen gp100 is currently being evaluated in the clinic (Rosenberg S A et al., *Nat Med* 4:321 (1998) and Kawakami Y et al., *J Immunol* 154:3961 (1995)). Numerous CTL epitopes restricted by the MHC class I alleles HLA-A2, -A3, -A11, -A24 and Cw8 have been reported (Kawakami Y et al., *J Immunol* 154:3961 (1995); Cox A L et al., *Science* 264:716 (1994); Tsai V. et al., *J Immunol* 158:1796 (1997); Kawashima I et al., 1998. *Int J Cancer* 78:518 (1998); Skipper J C et al., *J Immunol* 157:5027 (1996); Kawakami Y et al., *J Immunol* 161:6985 (1998); Robbins P F et al, *J Immunol* 159:303 (1997); and Castelli C et al, *J Immunol* 162:1739 (1999)). On the other hand, only one HTL epitope, which is restricted by the HLA-DR*0401 MHC class II allele, expressed in approximately one fourth of the population, has been described (Li K, et al., *Cancer Immunol Immunother* 47:32 (1998) and Touloukian C E et al., *J Immunol* 164:3535 (2000)).

SUMMARY

The invention provides gp100-derived polypeptides that contain a CTL epitope and an HTL epitope. Such gp100-derived polypeptides can be used to induce anti-tumor responses in melanoma patients. Because a concurrently induced HTL response can facilitate the induction and persistence of a CTL response, the materials and methods provided herein offer advantages over current approaches. In some embodiments of the invention, gp100-derived polypeptides bind more than one MHC class II allele (e.g., HLA-DR-53 or HLA-DQw6). Such polypeptides can be used more broadly to induce anti-tumor responses in melanoma patients.

In general, the invention features a polypeptide containing an HTL epitope and a CTL epitope, where the polypeptide is 13 to 30 amino acids long, and where the amino acid sequence of the polypeptide is at least 90% identical to a gp100 amino acid sequence. The polypeptide can contain an amino acid sequence as set forth in SEQ ID NO:1, 2, 3, 4, 5, 6, 7, 8, 9, 10, 11, 12, 13, 14, 15, or 16. The polypeptide can bind more than one MHC class II allele (e.g., HLA-DR-53 or HLA-DQw6). The CTL epitope can contain MLGTHTMEV (SEQ ID NO: 17), VSNDGPTLI (SEQ ID NO: 18), or ALNFPGSQK (SEQ ID NO: 19).

In another embodiment, the invention features a method for inducing an anti-tumor response in a mammal. The method includes administering a polypeptide to the mammal, where the polypeptide contains an HTL epitope and a CTL epitope, where the polypeptide is 13 to 30 amino acids long, and where the amino acid sequence of the polypeptide is at least 90% identical to a gp100 amino acid sequence. The polypeptide can contain an amino acid sequence as set forth in SEQ ID NO:1, 2, 3, 4, 5, 6, 7, 8, 9, 10, 11, 12, 13, 14, 15, or 16. The polypeptide can bind more than one MHC class II allele (e.g., HLA-DR-53 or HLA-DQw6). The CTL epitope can contain MLGTHTMEV (SEQ ID NO:17), VSNDGPTLI (SEQ ID NO:18), or ALNFPGSQK (SEQ ID NO:19).

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 7 is a table listing amino acid sequences.

DETAILED DESCRIPTION

Figure 1:
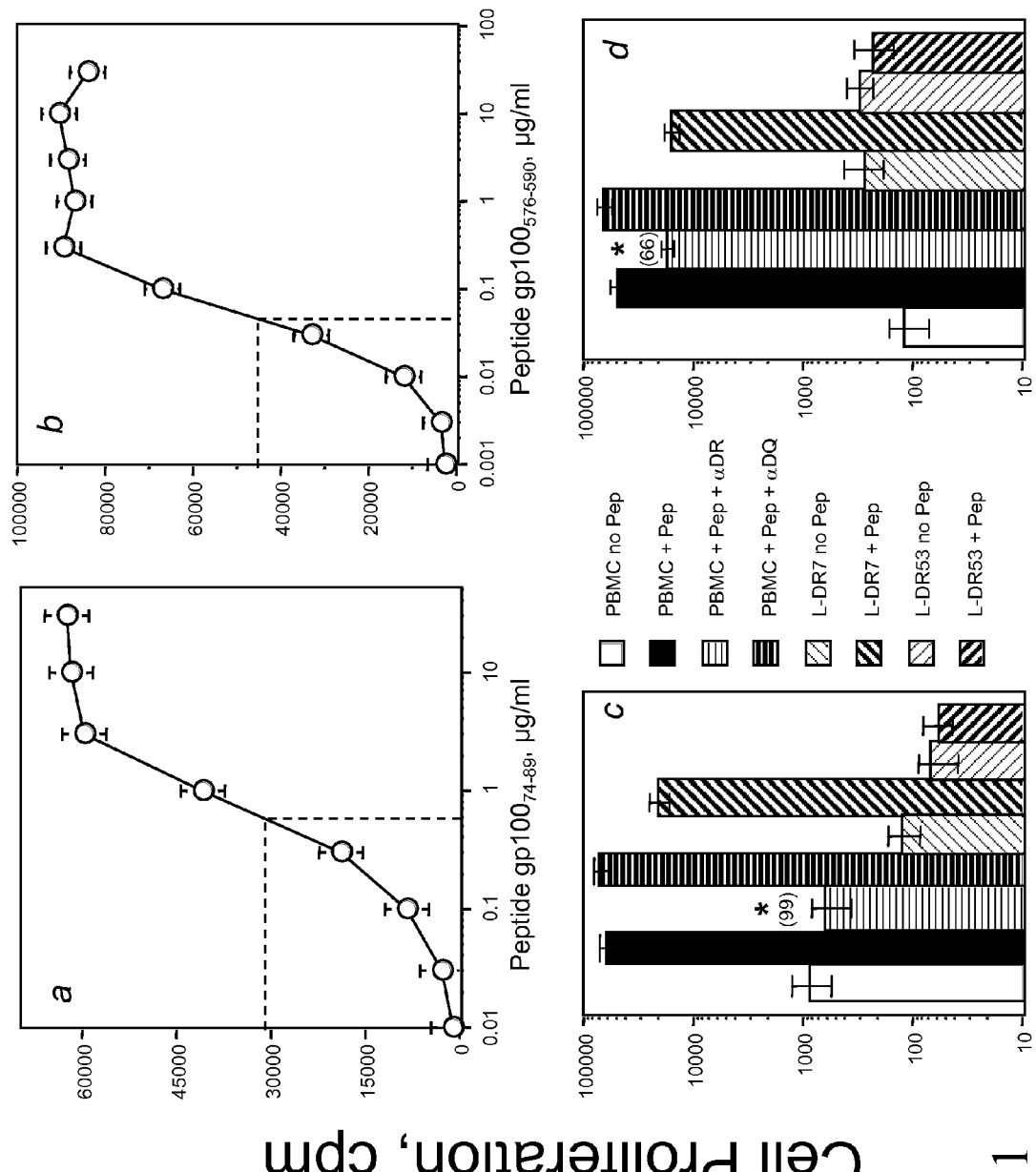
FIG. 1. HLA-DR7-restricted T-cell proliferative responses to gp100 polypeptides. HTL lines were selected by weekly stimulation using polypeptides gp100$_{74-89}$ (a and c) and gp100$_{576-590}$ (b and d). Polypeptide dose curve responses were performed to estimate the overall avidity of the HTL for their respective antigens (a and b). Dashed lines represent the polypeptide concentration required to obtain 50% of the maximal proliferation (~0.6 μg/ml for polypeptide gp100$_{74-89}$ and ~0.04 μg/ml for polypeptide gp100$_{576-590}$). MHC restriction analyses demonstrate that these HTL recognize their respective polypeptides in the context of the HLA-DR7 allele (c and d). In both cases the T cell proliferative responses to polypeptide presented by autologous PBMC were significantly inhibited by monoclonal anti-HLA-DR, "αDR" (but not anti-HLA-DQ, "αDQ") antibodies *=numbers in parentheses represent the % inhibition of proliferation induced by the antibodies. Mouse fibroblast lines (L-cells) transfected with human HLA-DR7 (but no those transfected with HLA-DR53) were efficient in presenting polypeptide to both HTL lines. Values shown are the means of triplicate determinations; bars, SD.

The invention provides polypeptides such as gp100-derived polypeptides that contain both an HTL epitope and a CTL epitope. The invention also provides methods for using such gp100 derived polypeptides to induce anti-tumor CTL and HTL responses in melanoma patients. Some polypeptides of the invention can bind to several MHC class II alleles, making them more broadly useful for inducing HTL and CTL anti-tumor responses in melanoma patients.

Polypeptides, and polypeptide segments, are contiguous sequences of 2 or more amino acids linked one to the other by peptide bonds. Polypeptides suitable for the present invention are between about 15 amino acids and about 30 amino acids long (e.g., about 15 to about 20 amino acids long, about 15 to about 25 amino acids long, about 20 to 25 amino acids long, and about 25 to 30 amino acids long).

Polypeptides of the invention are substantially pure (i.e., substantially free of other naturally occurring viral, bacterial, parasitic, tumor, or self polypeptides and fragments thereof). Polypeptides of the invention can have a CTL epitope (i.e., a polypeptide segment that can elicit a CTL response). Polypeptides of the invention can also have an HTL epitope (i.e., a polypeptide segment that can elicit an HTL response). In one embodiment, more than one MHC class II allele recognizes the polypeptide.

HTL and CTL epitopes of the polypeptides can be present in the configuration naturally found in a gp100 or gp100-derived melanoma tumor associated antigen. HTL and CTL epitopes of a polypeptide can also be present in a different configuration than naturally found in a gp100 or gp100-derived melanoma tumor associated antigen. HTL and CTL epitopes of a polypeptide can be discrete, where no amino acid of the HTL epitope is part of the CTL epitope. HTL and CTL epitopes of a polypeptide can also comprise common amino acids, where one or more amino acids of an HTL epitope is also part of a CTL epitope.

Polypeptides suitable for the compositions and methods of the present invention need not be identical to specific polypeptides disclosed. Thus, the polypeptides may be subject to various changes, such as insertions, deletions, and substitutions, either conservative or nonconservative, where such changes might provide for certain advantages in their use. Conservative substitutions result in the replacement of an amino acid residue with another that is biologically and/or chemically similar, e.g., one hydrophobic residue for another, or one polar residue for Ala; Val, Ile, Leu; Asp, Glu; Asn, Gln; Ser, Thr; Lys, Arg; and Phe, Tyr. Typically, the portion of the sequence that is intended to act as an CTL or HTL epitope will not differ by more than about 20% from the corresponding sequence of a native gp100 or gp100-derived antigen, except where additional amino acids may be added at either terminus for the purpose of modifying the physical or chemical properties of the polypeptide for, e.g., ease of linking or coupling, and the like.

Exemplary polypeptides include, without limitation:

| | |
|---|---|
| LAEMSTPEATGMTPA, | (SEQ ID NO: 1) |
| TEVISTAPVQMPTAE, | (SEQ ID NO: 2) |
| SLAVVSTQLIMPGQE, | (SEQ ID NO: 3) |

```
-continued

GILLVLMAVVLASLI,                    (SEQ ID NO: 4)

PVQMPTAESTGMTPE,                    (SEQ ID NO: 5)

GRAMLGTHTMEVTVY,                    (SEQ ID NO: 6)

GPTLIGANASFSIALN,                   (SEQ ID NO: 7)

QVVLQAAIPLTSCGS,                    (SEQ ID NO: 8)

PGPVTAQVVLQAAIP,                    (SEQ ID NO: 9)

KHFLRNQPLTFALQL,                    (SEQ ID NO: 10)

SLADTNSLAVVSTQLIMPGQE,              (SEQ ID NO: 11)

GILLVLMAVVLASLIYRRRLMK,             (SEQ ID NO: 12)

GILLVLMAVVLASLIYRRRLMKQDFSV,        (SEQ ID NO: 13)

VSNDGPTLIGANASFSIALN,               (SEQ ID NO: 14)

GPTLIGANASFSIALNFPGSQK,             (SEQ ID NO: 15)
AND

LEPGPVTAQVVLQAAIPLTSCGSS.       (SEQ ID NO: 16)
```

The polypeptides of the invention can be prepared in a wide variety of ways. Because of their relatively short size, the polypeptides can be synthesized in solution or on a solid automatic synthesizer in accordance with known protocols. See, for example, Stewart and Young, *Solid Phase Polypeptide Synthesis*, 2d. ed., Pierce Chemical Co. (1984); Tam et al., *J. Am. Chem. Soc.*, 105:6442 (1983); Merrifield, The Polypeptides, Gross and Meienhofer, ed., academic Press, New York, pp. 1-284 (1979).

Alternatively, recombinant DNA technology can be used wherein a nucleotide sequence which encodes a polypeptide of interest is inserted into an expression vector, introduced (e.g., by transformation or transfection) into an appropriate host cell, and cultivated under conditions suitable for expression. These procedures are generally known in the art, as described generally in Sambrook et al., *Molecular Cloning A Laboratory Manual*, Cold Spring Harbor Press, Cold Spring Harbor, N.Y. (1982), and Ausubel et al., (ed.) *Current Protocols in Molecular Biology*, John Wiley and Sons, Inc., New York (1987), and U.S. Pat. Nos. 4,237,224; 4,273,875; 4,431,739; 4,363,877; and 4,428,941, for example.

As the coding sequence for polypeptides of the length contemplated herein can be synthesized by chemical techniques, for example the phosphotriester method of Matteucci et al., *J. Am. Chem. Soc.* 103:3185 (1981), modification can be made simply by substituting the appropriate base(s) for those encoding the native polypeptide sequence. The coding sequence can then be provided with appropriate linkers and ligated into expression vectors commonly available in the art, and the vectors used to transform suitable hosts to produce the desired fusion polypeptide. A number of such vectors and suitable host systems are now available. For expression of the polypeptides, the coding sequence will typically be provided with operably linked start and stop codons, promoter and terminator regions and a replication system to provide an expression vector for expression in a suitable cellular host (e.g., bacterial, yeast or mammalian cells).

Polypeptides can be administered to mammals, particularly humans, to induce melanoma-specific anti-tumor CTL and HTL responses. Polypeptides can be administered intravenously, subcutaneously, intradermally, or intramuscularly, topically, orally or locally. Compositions for parenteral (i.e., intravenous, subcutaneous, intradermal, or intramuscular) administration comprise an HTL and CTL stimulatory polypeptide dissolved or suspended in an acceptable carrier, preferably an aqueous carrier. A variety of aqueous carriers can be used, e.g., water, buffered water, 0.4% saline, 0.3% glycine, hyaluronic acid, and the like. These compositions can be sterilized by conventional sterilization techniques. The resulting aqueous solutions can be packaged for use as is or lyophilized—the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, methanol, and dissolving agents such as DMSO. The amount HTL and CTL stimulatory polypeptide in a pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected. Actual methods for preparing parenterally administrable compounds will be known or apparent to those skilled in the art and are described in more detail in for example, *Remington's Pharmaceutical Sciences*, 17$^{th}$ ed., Mack Publishing Company, Easton, Pa. (1985), which is incorporated herein by reference.

Polypeptides can also be administered via liposomes, which can target the polypeptides to a particular tissue, such as lymphoid tissue, or targeted selectively to tumor cells, as well as increase the half-life of the polypeptide composition. Liposomes can include, without limitation, emulsions, foams, micelles, isoluble monolayers, liquid crystals, phospholipid dispersions, lamellar layers, and the like. In these preparations, the polypeptide to be delivered can be incorporated as part of a liposome, alone or in conjunction with a molecule which bonds to, e.g., a receptor prevalent among lymphoid cells, such as monoclonal antibodies which bind to the CD45 antigen, or with other therapeutic or immunogenic compositions. Thus, liposomes filled with a desired polypeptide can be directed to the site of lymphoid cells, where the liposomes then deliver the selected therapeutic/immunogenic polypeptide compositions. Liposomes for use in the invention can be formed from standard vesicle-forming lipids, which generally include neutral and negatively charged phospholipids and a sterol, such as cholesterol. The selection of lipids is generally guided by consideration of, e.g., liposome size and stability of the liposomes in the blood stream. A variety of methods are available for preparing liposomes, as described in e.g., Szoka et al., *Ann. Rev. Biophys. Bioeng.* 9:467 (1980), U.S. Pat. Nos. 4,235,871; 4,501,728; 4,837,028; and 5,019,369. For targeting to the immune cells, a ligand to be incorporated into the lipsome can include, e.g., antibodies or fragments thereof specific for cell surface determinants of the desired immune system cells. A liposome suspension containing a polypeptide can be administered, for example, intravenously, locally, topically, in a dose that can vary according to, among other things, the manner of administration, the polypeptide being delivered, and the progression of the disease.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of the active ingredient, that is, one or more polypeptide compositions of the invention, and more preferably at a concentration of 25%-75%.

Figure 2:
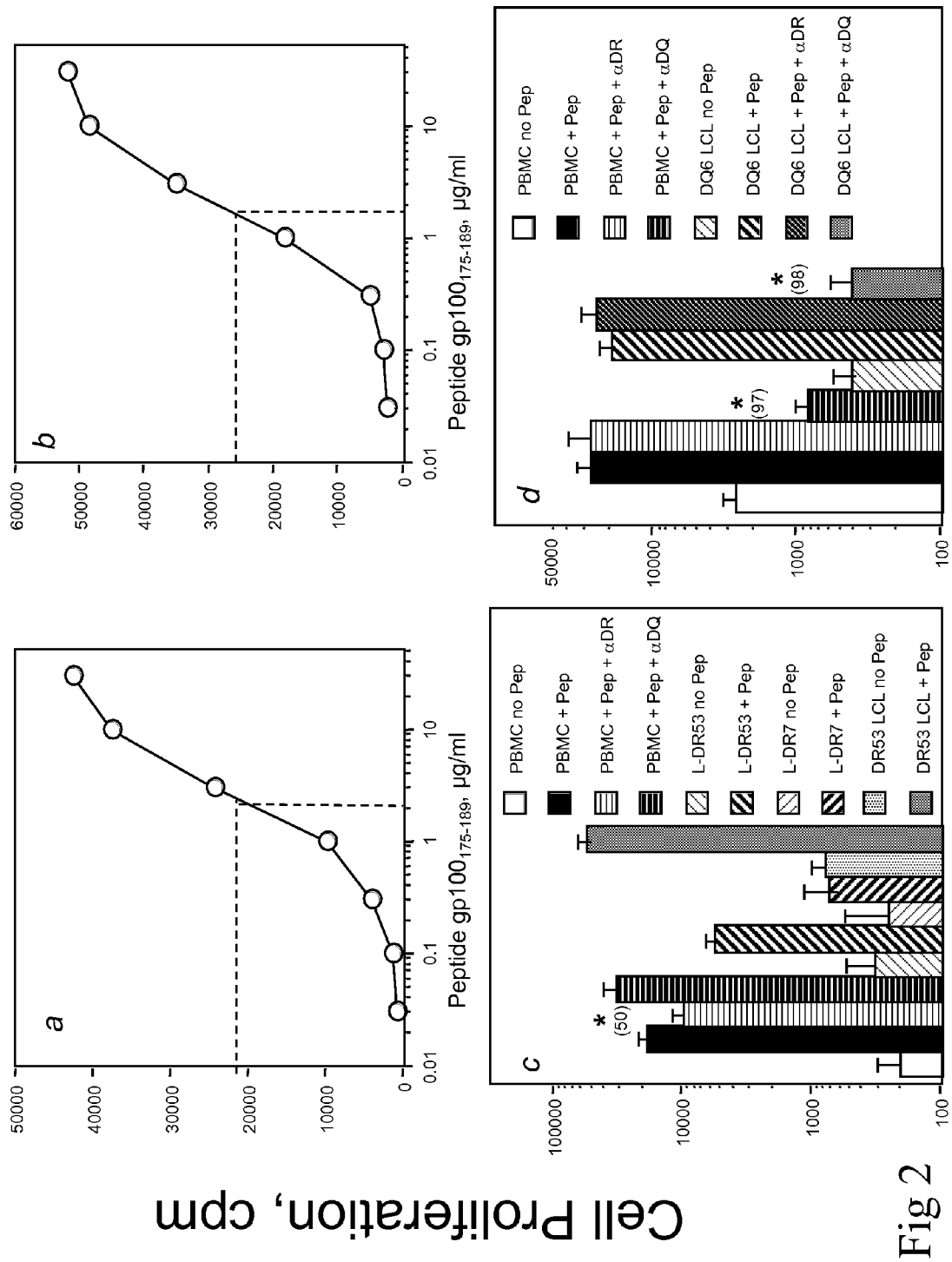
FIG. 2. Polypeptide gp100$_{175-189}$ can be recognized by HTL in the context of HLA-DR53 (a and c) or HLA-DQw6 (b and d). Polypeptide dose curve responses were performed to estimate the overall avidity of these HTL for polypeptide gp100$_{175-189}$ (a and b). Dashed lines represent the polypeptide concentration required to obtain 50% of the maximal proliferation (~2 µg/ml for both HTL lines). MHC restriction analyses demonstrate that one of the HTL recognize polypeptide gp100$_{175-189}$ in the context of the HLA-DR53 allele (panel c) and the other one in the context of HLA-DQw6 (panel d). In both cases the T cell proliferative responses to polypeptide presented by autologous PBMC were significantly inhibited by monoclonal anti-HLA-DR (c) or -HLA-DQ (d) antibodies *=numbers in parentheses represent the % inhibition of proliferation. Mouse fibroblast lines (L-cells) transfected with human HLA-DR53 but not with HLA-DR7 were efficient in presenting polypeptide gp100$_{175-189}$ to one of the HTL lines (c). In addition an allogeneic lymphoblastoid cell line (LCL) only sharing HLA-DR53 with the T cells was also efficient in stimulating this cell line (c). Allogeneic LCL that only share HLA-DQw6 can present polypeptide gp100$_{175-189}$ to the second HTL line (d). Values shown are the means of triplicate determinations; bars, SD.

For aerosol administration, an HTL and CTL stimulatory polypeptide can be provided in finely divided form along with a surfactant and propellant. Typical percentages of polypeptides are 0.01%-20% by weight, preferably 1%-10%. The surfactant is typically nontoxic and is typically soluble in the propellant. Representative surfactants include esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. Surfactant can constitute 0.1%-20% by weight of the composition, preferably 0.25-5%. The balance of the composition is ordinarily propellant. A carrier such as lecithin, for one example, can also be included for intranasal delivery.

An HTL and CTL stimulatory polypeptide can be introduced into a mammalian host, including humans, linked to its own carrier or as a homopolymer or heteropolymer of active polypeptide units. Such a polymer can elicit increase immunological reaction and, where different polypeptides are used to make up the polymer, the additional ability to induce antibodies and/or T cells that react with different antigenic determinants of the melanoma tumor. Useful carriers known in the art include, for example, thyroglobulin, albumins such as human serum albumin, tetanus toxoid, polyamino acids such as poly(D-lysine:D-glutamic acid), influenza polypeptide, and the like. Adjuvants such as incomplete Freunds adjuvant, GM-CSF, aluminum phosphate, aluminum hydroxide, alum, or montanide can also be used in the administration of an HTL and CTL stimulatory polypeptide.

The invention will be further described in the following examples, which do not limit the scope of the invention described in the claims.

EXAMPLES

Example 1

Synthetic Polypeptides and Algorithm Analysis

Potential HLA-DR promiscuous $CD4^+$ T-cell epitopes capable of binding to more than one MHC class II allele were selected from the amino acid sequence of the gp100 antigen using the algorithm tables for three HLA-DR alleles (DRB1*0101, DRB1*0401, and DRB1*0701) published by Southwood, et al (*J Immunol* 160:3363 (1998). A computer program based on Microsoft Excel was created for each of the HLA-DR alleles. For each position of a 9-mer core, a value was assigned for each possible specific amino acid taking the tables published by Southwood, et al (*J Immunol* 160:3363 (1998). The computer program calculated the average binding (ARB) values for each possible 9mer of the gp 100 sequence. The higher the ARB value, the more likely the polypeptide will bind to the corresponding HLA-DR allele. The data in FIG. 7 demonstrate that the sequences, ARB values for each allele, ranks and rank sum values for the top 10 candidate polypeptides. Polypeptides that displayed high ARB values and were proximal with known CTL epitopes were synthesized and purified as described. The purity (>95%) and identity of polypeptides were determined by mass spectrometry.

Example 2

In Vitro Induction of Antigen-Specific HTL using Synthetic Polypeptides

Polypeptides $gp100_{74-89}$, $gp100_{175-189}$ and $gp100_{576-590}$ were tested for their capacity to stimulate $CD4^+$ T cells obtained from four healthy, MHC-typed individuals in primary in vitro cultures using polypeptide-pulsed autologous dendritic cells (DC). The method used to generate tumor antigen-reactive HTL lines and clones using polypeptide-stimulated peripheral blood mononuclear cells (PBMC) was recently described in detail (Kobayashi H et al., *Cancer Res* 60:5228 (2000)). Briefly, DC were generated in tissue culture from adherent monocytes that were cultured for 7 days in the presence of GM-CSF and IL-4. A total of ($1\times10^4$) polypeptide-pulsed DC (10 μg/ml for 2 hr) were irradiated (4,200 rad) and co-cultured with $3\times10^4$ autologous purified $CD4^+$ T cells (using magnetic microbeads from Miltenyi Biotech) in each well of a 96-round bottom well culture plate. Seven days later, the cultures were restimulated with polypeptide-pulsed irradiated autologous PBMC and two days later, human rIL-2 was added at a final concentration of 10 IU/ml. After 7 days, the microcultures were tested for their proliferative responses to polypeptide as described below. Those micro-wells showing a proliferative response to polypeptide (at least 2.5 fold over background) were expanded in 24 or 48-well plates by weekly restimulation with polypeptides and irradiated autologous PBMC. In some instances T-cell lines were cloned by limiting dilution and used for further studies. Culture medium for all procedures consisted of RPMI-1640 supplemented with 5% human male AB serum, 0.1 mM MEM nonessential amino acids, 1 mM sodium pyruvate, 2 mM L-glutamine, and 50 μg/ml gentamicin.

Polypeptides $gp100_{74-89}$ and $gp100_{576-590}$ induced proliferative responses in $CD4^+$ T-cells that were restricted by the HLA-DR7 allele (FIG. 1). In both cases, the T-cells responded to polypeptide presented by autologous PBMC in a dose dependent manner (FIGS. 1*a* and 1*b*). The affinity of T-cell response to polypeptide $gp100_{576-590}$, however, appeared to be higher (~15 fold) than the response to polypeptide $gp100_{74-89}$ as determined by the amount of polypeptide required to achieve 50% of maximal proliferative response. The response of both T-cell lines were restricted by HLA-DR7 molecules as determined by the capacity of DR7-transfected L-cells to present polypeptide to the T-cells and by the capacity of anti-DR antibodies (but not anti-DQ) to block the T-cell proliferative responses (FIGS. 1*c* and 1*d*). Thus, $gp100_{74-89}$ and gp $100_{576-590}$ trigger HTL restricted by the HLA-DR7 allele, which is expressed in approximately 26% of Caucasians. Although both of these polypeptides were selected as potential "promiscuous" epitopes, they were not able to trigger HTL restricted by other alleles such as HLA-DR1 or -DR4. Nevertheless, given the limited number of attempts to induce these responses (2 experiments with cells from 2 donors), these epitopes may indeed have some degree of promiscuity.

Two separate T-cell clones reactive with polypeptide $gp100_{175-189}$ were isolated from two normal individuals and studied in more detail for their proliferative response to antigen. The data presented in FIG. 2 demonstrates that both of the T-cell clones recognized polypeptide in a dose dependent way with similar levels of affinity (FIGS. 2*a* and 2*b*). Studies performed to determine the HLA restriction elements for these clones indicated that in one case the response to polypeptide gp100$_{175-189}$ was restricted by HLA-DR53 (FIG. 2c) and in the other case by HLA-DQw6 (FIG. 2d). Thus, gp100$_{175-189}$ represents a promiscuous HTL epitope capable of eliciting HTL responses restricted by HLA-DR53 and -DQw6. Since approximately one half of the population expresses one or both of these MHC alleles, this polypeptide could be useful for eliciting anti-tumor HTL responses to melanoma in a large number of tumor patients.

Example 3

Antigen-Specific Proliferative Response of T Cells

Recognition of naturally processed antigen by polypeptide-reactive T-cells can be an important parameter to determine whether a predicted T-cell epitope can be used to elicit an immune response against tumor cells. HTL may recognize polypeptide/MHC class II complexes directly on tumor cells that are MHC class II positive and as a consequence the T-cells will become activated and produce cytokines that provide help to CTL or cytokines that may inhibit tumor cell growth.

T cells ($3\times10^4$/well) were mixed with irradiated APC in the presence of various concentrations of antigen (polypeptides, tumors or tumor lysates), in 96-well culture plates. APC consisted of either PBMC ($1\times10^5$/well), HLA-DR-expressing L-cells ($3\times10^4$/well), EBV-LCL or melanoma tumor cells ($3\times10^4$/well), pretreated with IFN-γ (500 U/ml for 48 h) to enhance MHC expression. Proliferation assays were incubated at 37° C. in a 5% $CO_2$ incubator for 72 h and during the last 16 h, each well was pulsed with 0.5 μCi/well of [$^3$H]-thymidine (Amersham Pharmacia Biotech, Piscataway, N.J.). In some cases, culture supernatants were collected before the addition of [$^3$H]-thymidine for the determination of lymphokine production using ELISA kits (Pharmingen, San Diego, Calif.). The radioactivity incorporated into DNA, which correlates with cell proliferation, was measured in a liquid scintillation counter after harvesting the cell cultures onto glass fiber filters. To determine MHC restriction molecules involved in antigen presentation, blocking of the antigen-induced proliferative response was investigated by adding anti-HLA-DR mAb L243 (IgG2a, prepared from hybridoma supernatants obtained from the (American Type Culture Collection) or anti-HLA-DQ mAb SPVL3 (IgG2a, Beckman Coulter, Inc., Fullerton, Calif.). Both antibodies were used at a final concentration of 10 μg/ml throughout the 72 h assay. The specificity of these antibodies and their capacity to specifically inhibit T helper responses has been determined in our laboratory in numerous occasions. All assessments of proliferative responses were carried out at least in triplicate and results correspond to the means. The stimulation index (SI) was calculated by dividing the mean radioactivity (cpm) obtained in the presence of antigen by the mean radioactivity (cpm) obtained in the absence of antigen but in the presence of APC.

Figure 3:
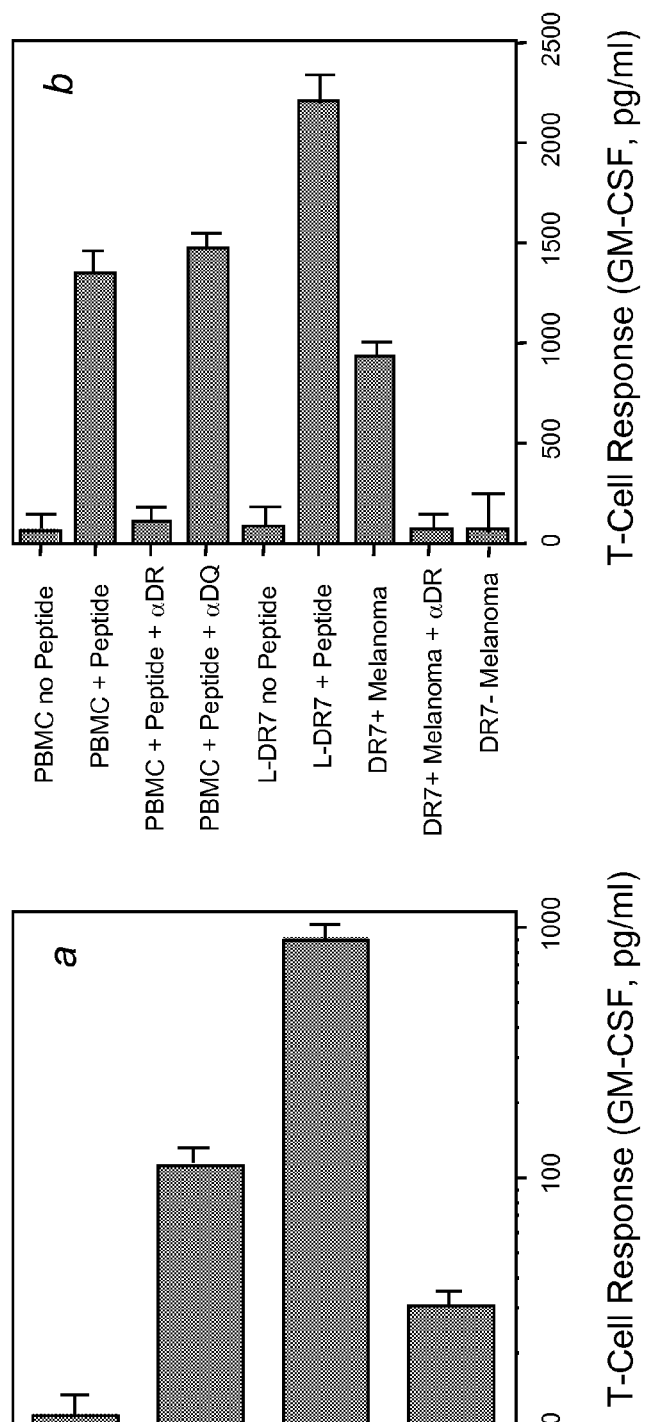
FIG. 3. HLA-DR7-restricted HTL specific for polypeptide gp100$_{74-89}$ can recognize naturally processed antigen. Panel a: Autologous (DR7$^+$) PBMC are efficient in stimulating HTL responses (assessed by the production of GM-CSF, measured by ELISA) by presenting polypeptide gp100$_{74-89}$ or a lysate from gp100$^+$ melanoma cells (697 mel, DR7 negative) but not a lysate from Jurkat cells. Panel b: Production of GM-CSF by HTL is also observed with polypeptide-pulsed APC (autologous PBMC or L-DR7 cells) or with intact DR7 positive melanoma cells (HT-144), but not with a DR7 negative melanoma (888 mel). These responses are inhibited by anti-DR monoclonal antibodies (αDR). Values shown are the means of triplicate determinations; bars, SD. These experiments were repeated at least three times with similar results.

FIG. 3a demonstrates that the HLA-DR7-restricted T-cell line (10B1) induced with polypeptide gp100$_{74-89}$ was efficient at recognizing tumor cell lysates from a gp100$^+$ melanoma tumor (697 mel), but not control tumor lysates (Jurkat), presented by autologous APC. For these experiments, the lysates were prepared using a DR7 negative melanoma (697 mel) to ensure that the autologous APC were indeed capturing the gp100 antigen from the lysate to process and present the epitope to the helper T-cells. Furthermore, these HTL were also effective in recognizing antigen presented directly by HLA-DR7$^+$ melanoma tumors (HT-144), and this recognition could be inhibited with anti-HLA-DR antibodies (FIG. 3b). These results indicate that the T-cell epitope represented by polypeptide gp100$_{74-89}$ is not only processed by APC from tumor cell lysates but is also expressed on MHC class II molecules on melanoma cells. A similar analysis was performed using the HTL line induced with polypeptide gp100$_{576-509}$, but in this case T-cell responses could not be detected using tumor lysates or intact melanoma cells.

Figure 4:
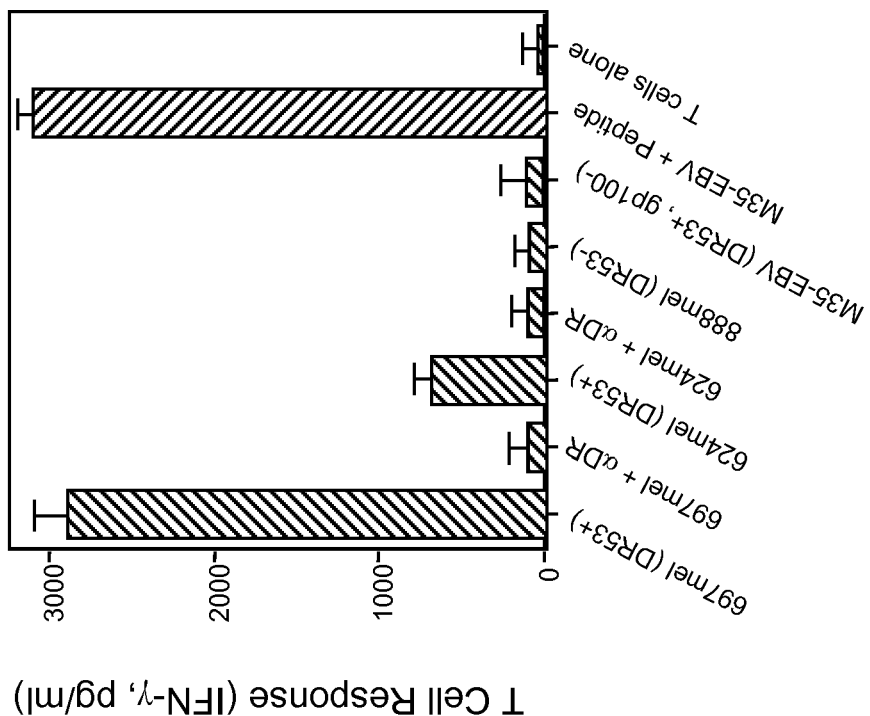
FIG. 4. Recognition of naturally processed antigen by gp100$_{175-189}$-specific, HLA-DR53-restricted HTL. A T-cell clone derived from 5D10 was tested for its capacity IFN-γ when challenged with intact DR53$^+$ melanomas (697 mel and 624 mel). Production of IFN-γ was inhibited by anti-DR antibodies and could not be detected using DR53 negative melanoma cells (888 mel). Controls shown are the production of IFN-γ by HTL stimulated with DR53 positive lymphoblastoid cells (M35-EBV) in the presence and absence of polypeptide gp100$_{175-189}$. Values are the means of triplicate determinations; bars, SD.
Figure 5:
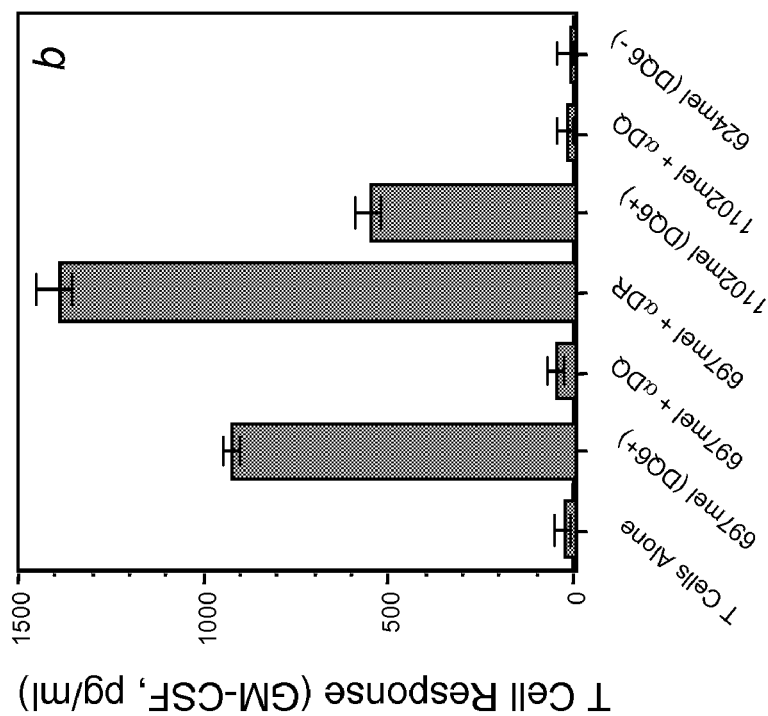
FIG. 5. gp100$_{175-189}$-specific CD4$^+$ T-cells restricted by HLA-DQw6 can also recognize naturally processed antigen. Panel a: autologous PBMC present synthetic polypeptide or melanoma (gp100$^+$) lysates to HTL resulting in the production of GM-CSF. HTL response to a lysate from a gp100 negative cell line (Jurkat) was significantly lower. Panel b: Intact HLA-DQw6 positive melanomas can induce the production of GM-CSF by antigen-specific HTL. Results demonstrate that this response is inhibited by anti-DQ (αDQ) monoclonal antibodies, but not by anti-DR antibodies. Values shown are the means of triplicate determinations; bars, SD.
Figure 5:
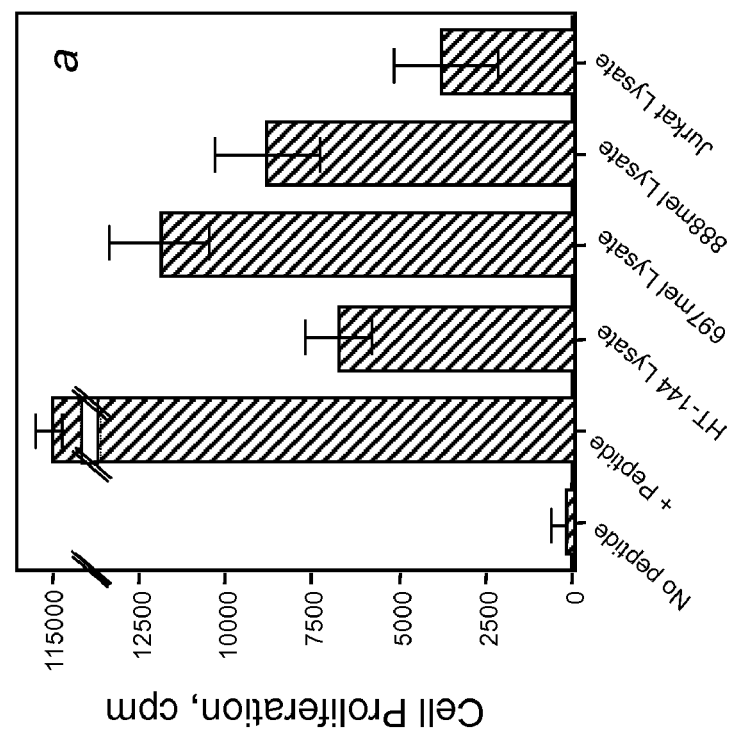

The two HTL lines reactive with polypeptide gp100$_{175-189}$ were also tested for their ability to recognize naturally processed antigen. HTL clone 5D10 (HLA-DR53-restricted) was unable to recognize melanoma cell lysates presented by autologous APC. However, the HTL were very effective in recognizing intact HLA-DR53 positive melanomas, but not DR53 negative melanomas or DR53 positive lymphoblastoid cells that do not produce gp100$^+$ (M35-EBV), unless pulsed with polypeptide (FIG. 4). In addition, the recognition of gp100$^+$ melanoma tumor cells by these HTL was inhibited with anti-HLA-DR antibodies (FIG. 4), confirming that this interaction requires the presentation of polypeptide by MHC class II molecules. A T-cell clone (4D16) derived from the HLA-DQw6-restricted line was studied for its ability to recognize processed antigen derived from tumor cell lysates presented by APC or intact class II positive melanomas. The results shown in FIG. 5a demonstrate that these HTL were capable of reacting with antigen derived from melanoma lysates presented by autologous APC. In addition, this HTL clone was also quite effective in recognizing antigen directly on DQw6$^+$ melanomas (FIG. 5b). Thus, it appears that the T-cell epitope represented by polypeptide gp100$_{175-189}$ can be found expressed on both HLA-DR53 and HLA-DQw6 molecules on MHC class II melanomas.

Thus, HTL reactive to gp100$_{175-189}$ and HTL reactive to gp100$_{74-89}$ were capable of recognizing naturally processed antigen in MUC class II positive melanomas or in APC fed with tumor lysates. On the other hand, HTL that were induced using polypeptide gp100$_{576-590}$ did not proliferate or produce lymphokines when interacting with MHC class II positive melanomas or tumor lysates presented by APC.

Example 4

Antigen-Specific Cytotoxicity Assays

In some cases, HTL exhibit cytotoxicity towards antigenic MHC class II tumors. See, Manici et al., *J Exp Med* 189:871 (1999); Fujita et al., *Eur J Immunol* 28:305 (1998); Zarour et al., *Cancer Res* 60:4946 (2000); Touloukian et al., *J Immunol* 164:3535 (2000); Zarour et al., *Proc Natl Acad Sci USA* 97:400 (2000); Yasukawa et al., *Blood* 92:3355 (1998). Polypeptide gp100$_{175-189}$, which generated DR53- and DQw6-restricted HTL capable of recognizing naturally processed antigen, includes a potent HLA-A2-restricted CTL epitope (gp100$_{177-186}$). Polypeptide gp100$_{177-186}$ is very effective in inducing anti-tumor CTL responses by in vitro immunization of PBMC from normal individuals using polypeptide-pulsed DC.

The capacity of HTL lines and clones to kill tumor cells expressing the appropriate polypeptide/MHC complexes was evaluated using the JAM assay (Matzinger P, *J Immunol Methods* 145:185 (1991)), which measures the DNA retained by target living cells after incubation with effector T-cells. Briefly, target cells were labeled with of [$^3$H]-thymidine for 18 hrs in tissue culture. After washing and counting the cells, they were incubated at various effectors to target ratio in 96-well round-bottomed plates for 36 hours. The cultures were then harvested onto glass fiber filters, and the amount of radioactivity retained in DNA is measured in a scintillation counter. The percent cytotoxicity was calculated by the ratio of cpm obtained in the absence of T-cells over the cpm obtained in the presence of different amounts of T-cells X 100. All determinations were done in triplicates.

Figure 6:
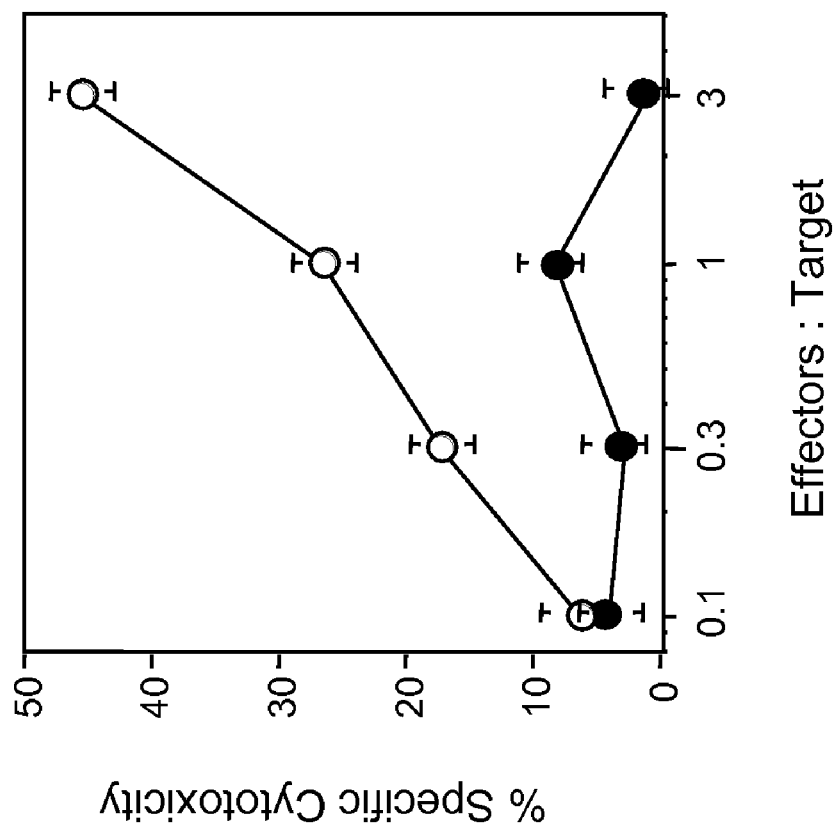
FIG. 6. Cytolytic activity against melanoma cells of gp100$_{175-189}$-specific CD4$^+$ T-cells. The HLA-DQw6-restricted HTL clone was tested for its ability to kill melanoma cells using the JAM assay as described in "Materials and Methods". Target cells tested were: 1102 mel (open circles) and M35 EBV-LCL (closed circles).

FIG. 6 demonstrates that HLA-DQw6-restricted HTL that react with polypeptide $gp100_{175-189}$ display high levels of cytotoxicity against a DQw6 positive melanoma cell line. Thus, polypeptide $gp100_{175-189}$ can be used to elicit anti-tumor HTL and CTL responses in patients expressing HLA-DR-53 or HLA-DQw6 class II alleles.

The other gp100-reactive HTL lines exhibited lower levels of cytotoxicity against melanoma cell lines. Polypeptide $gp100_{74-89}$, which stimulated an HLA-DR7-restricted HTL response, partially overlaps (in its carboxyl end) with another CTL epitope, but this one is restricted by the HLA-A3 and -A11 alleles ($gp100_{87-95}$; ALNFPGSQK; SEQ ID NO:19). Thus, a synthetic polypeptide of 22 residues ($gp100_{74-95}$) can be used to elicit anti-tumor CTL and HTL responses in patients expressing HLA-A3 (or -A11) and HLA-DR7. Polypeptide $gp100_{74-89}$ also overlaps in its amino terminal end with another CTL epitope ($gp100_{70-78}$), this one being restricted by HLA-Cw8. Thus, a synthetic polypeptide of 20 residues ($gp100_{70-89}$) can be used to elicit anti-tumor CTL and HTL responses in patients expressing HLA-Cw8 and HLA-DR7.

Example 5

Clinical Study

To assess polypeptides of the invention, the following study is performed. Metastatic melanoma HLA-A2 positive patients are immunized with an immunodominant peptide derived from gp-100. The immunization is performed in the presence of GM-CSF and IFA as immune-adjuvants and goals include quantification of specific CTL responses and observation for therapeutic efficacy. Of particular interest is the comparison of the efficacy of immunization in patients that share the class II HLA antigens specific for the peptide relative to those that do not. This will provide preliminary data for the need of T helper cell participation with shared epitopes recognized by CTLs.

In the proposed study, the efficacy of immunization measured by the following is examined: specific cytotoxic T lymphocyte (CTL) activity against melanoma tumor cells; frequency of peptide-specific T cells determined by fluorescent tetramer analysis; levels of activation of tetramer-specific T cells measured by cellular cytokine production; in vivo delayed type hypersensitivity reactions to peptide challenge after immunization; and, whenever possible, measurement of numbers/function of tumor related/infiltrating T cells. We will collect preliminary data relating to the efficacy of treatment is collected by following changes in tumor size for the duration of the clinical trial.

Goals
  Determine the immunologic effects of immunization using a HLA class I and II specific gp-100-derived peptide suspended in IFA in the presence or absence of GM-CSF.
  Define the safety and toxicity profile of the immunization protocol.
    Collect preliminary data on:
      Therapeutic efficacy as it relates to parameters of immune function in patients with stage 1V malignant melanoma.
      Compare immunization efficacy of patients that share the HLA-DR53 and/or DQw6 haplotypes versus those who do not.
Patient Eligibility
  Required Characteristics
  Age ≧18 years.
  HLA-A2 positive.
  Histologic proof of measurable stage 1V malignant melanoma.
  Melanoma positive for gp-100.
  Laboratory values obtained ≦14 days prior to registration:
  Absolute Neutrophil Count (ANC)≧1500×10$^9$/L
  Platelets ≧100,000×10$^9$/L
  Hemoglobin >9.0 g/dL
  AST ≦3×ULN
  Alkaline phosphatase ≦3×ULN
  Creatinine ≦2.5×ULN
  Ability to provide informed consent.
  Willingness to return to clinic for follow-up.
  Life expectancy ≧12 weeks.
  ECOG performance status 0, 1 or 2.
  Contraindications
  Uncontrolled or current infection
  Known standard therapy for the patient's disease that is potentially curative or proven capable of extending life expectancy.
  Known allergy to vaccine or adjuvant components.
  Any of the following prior therapies with interval since most recent treatment:
  Chemotherapy ≦4 weeks
  Mitomycin C/nitrosoureas ≦6 weeks
  Biologic therapy ≦4 weeks
  Radiation therapy ≦4 weeks
  Radiation to >25% of bone marrow
  Failure to fully recover from effects of prior chemotherapy regardless of interval since last treatment.
  Other concurrent chemotherapy, immunotherapy, or radiotherapy.
  New York Heart Association classification III or IV (Table II).
  Seizure disorder.
  Any of the following as this regimen may be harmful to a developing fetus or nursing child:
  Pregnant women
  Nursing women
  Women of childbearing potential or their sexual partners who are unwilling to employ adequate contraception (condoms, diaphragm, birth control pills, injections, intrauterine device [IUD], surgical sterilization, subcutaneous implants, or abstinence, etc.)
  Known immune deficiency, as patients with known immune deficiencies will likely not be able to mount an immune response to the study vaccine.
  Active psychiatric disorder requiring anti-psychotic medications.
  Known central nervous system metastases or carcinomatous meningitis.
  History of other malignancy in last 5 years with the exception of basal cell or squamous cell carcinoma of the skin treated with local resection only (it is impossible to predict the effect of study treatment on other, potentially dormant malignant diseases)

TABLE II

NEW YORK HEART ASSOCIATION CLASSIFICATIONS
Clinical Evaluation of Functional Capacity of Patients
with Heart Disease in Relation to Ordinary Physical Activity

| Class | Cardiac Symptoms | Limitations | Need for Additional Rest* | Physical Ability to work** |
|---|---|---|---|---|
| I | None | None | None | Full time |
| II | Only moderate | Slight | Usually only slight or occasional | Usually full time |
| III | Defined, with less than ordinary activity | Marked | Usually moderate | Usually part time |
| IV | May be present even at rest, and any activity increases discomfort | Extreme | Marked | Unable to work |

*To control or relieve symptoms, as determined by the patient, rather than as advised by the physician.
**At accustomed occupation or usual tasks.
Reference: Bruce, R. A.: Mod. Concepts Cardiovasc. Dis. 25: 321, 1956. (Modified from New York Heart Association, 1953).

Test Schedule

| Tests and procedures | ≦14 days prior to registration | Prior to each cycle | Prior to cycle 7 treatment | Week 24 | Long-term follow-up q3 months until month 24 post registration |
|---|---|---|---|---|---|
| History and exam, weight, performance status | X | X | X | X | X |
| Height | X | | | | |
| Tumor measurement/evaluation | X | X[4] | X | X | X |
| Hematology group WBC, ANC, Hgb, PLT | X | X | X | X | X |
| Chemistry group AST, LDH, Alk Phos, Creat, K, Na) | X | X | X | X | X |
| Injection site skin reaction | | X[6] | | X[6] | |
| DTH anergy panel | R | | R | | |
| DTH tumor antigens | R | | R | | |
| Immunology studies[1] | R | R | | | |
| HLA typing | R[5] | | | | |
| Gp-100 tumor stain | R[5] | | | | |
| Lymph node aspiration[2] | | | R | | |
| Serum pregnancy test[3] | R | | | | |
| Picture of all injection sites documenting local skin reactions[7] | | R | | R | |

[1] 100 cc of peripheral blood will be collected for immunologic studies.
[2] Only if immunization site regional lymph node is clinically enlarged
[3] For women of childbearing potential only. Must be done ≦7 days prior to registration
[4] Before treatments for cycles # 3 and 6.
[5] May be done up to 6 months before registration.
[6] Measure vaccine injection sites maximum diameter of erythema and induration (i.e. gp-100 (Feb. 12, 2001): E = 5.3 cm, I = 2.0 cm). Code each vaccine site in sequence of injection (site of 1st injection, etc.) and record erythyma/induration for each site at each time point. See Appendix IV for documentation form.
[7] Optional.
R Research funded.

Stratification Factor:
  Dominant disease: Visceral vs. Non-visceral.
  HLA-DR53 and/or DQw6 positive vs negative.

Registration/Randomization Procedures
  Prior to discussing protocol entry with the patient, determine for dose level.
  Register patient.
  Obtain signed consent form.
  Confirm patient eligibility and the existence of a signed consent form.
  Treatment assignment is calculated using a dynamic allocation procedure that balances the marginal distributions of the stratification factor among the treatment groups. The stratification factor is defined in Section 5.0.
  Treatment on this protocol commences at the clinic under the supervision of a medical oncologist.
  Treatment begins prior to registration and begins within 3 days of registration.
  Pretreatment tests are completed within the guidelines specified on the test schedule.
  All baseline symptoms are documented and graded on the oncology record.

Protocol Treatment

Treatment groups:

| Group | Peptide (µg) in IFA | GM-CSF (µg) | Retreat |
|---|---|---|---|
| A | 1000 | 0 | Day 1 of wk 0, 3, 6, 9, 12, 15, 18 and 24 |
| B | 1000 | 62.5 | Day 1 of wk 0, 3, 6, 9, 12, 15, 18 and 24 |
| C | 1000 | 100 | Days 1-5 of wk 0, 3, 6, 9, 12, 15, 18 and 24 |

Treatment Schedule:

Group A: (1 treatment cycle = 3 weeks)

| Day | Agent | Dose (µg) | Route | Re-treat |
|---|---|---|---|---|
| 0 | peptide | 1000 | s.q. | Repeat entire cycle every 3 weeks (see table 7.1) |

Group B: (1 treatment cycle = 3 weeks)

| Day | Agent | Dose (µg) | Route | Re-treat |
|---|---|---|---|---|
| 1 | GM-CSF peptide | 62.5 1000 | s.q. | Repeat entire cycle every 3 weeks (see table 7.1) |

Group C: (1 treatment cycle = 3 weeks)

| Day | Agent | Dose (µg) | Route | Re-treat |
|---|---|---|---|---|
| 1 | GM-CSF peptide | 100 1000 µg | s.q. s.q. | Repeat entire cycle every 3 weeks (see table 7.1) |

Ten patients are randomly assigned to receive one of the three treatment combinations.
Doses are not escalated in any individual patient.

Dosage Modification Based on Toxicity
Use Common Toxicity Criteria (CTC)
Version 2.0 unless otherwise specified.

| CTC Category | Toxicity | peptide | GM-CSF |
|---|---|---|---|
| BASED ON INTERVAL TOXICITY | | | |
| Blood/Bone Marrow | Hematologic: ANC <1,500 or PLT <100,000 | ↓ by 50% | No change |
| All | Non-hematologic: | | |
| | Grade 3 | ↓ by 50% | ↓ by 50% |
| | Grade 4 | Stop Rx | Stop Rx |
| Pain | Bone pain (grade 3, 4) | No change | ↓ by 50% |
| | Myalgia/arthralgia (grade 3, 4) | ↓ by 50% | ↓ by 50% |
| Skin | Grade 3 | ↓ by 50% | ↓ by 50% |
| | Grade 4 | Stop Rx | Stop Rx |
| AT SCHEDULED RETREATMENT | | | |
| Blood/Bone Marrow | Hematologic: ANC <1,500 or PLT <100,000 | Hold and ↓ by 50%[1] | No change |
| All | Non-hematologic: | | |
| | Grade 3 | Hold and ↓ by 50%[1] | Hold and ↓ by 50%[1] |
| | Grade 4 | Stop Rx | Stop Rx |
| Pain | Bone pain (grade 3, 4) | Hold and ↓ by 50%[1] | Hold and ↓ by 50%[1] |
| | Myalgia/arthralgia (grade 3, 4) | Hold and ↓ by 50%[1] | Hold and ↓ by 50%[1] |
| Skin | Grade 3 | Hold and ↓ by 50%[1] | Hold and ↓ by 50%[1] |
| | Grade 4 | Stop Rx | Stop Rx |

[1]Hold treatment until level of toxicity is grade 2 or less before proceeding with therapy at 50% decreased dose. If patient does not recover to grade 2 toxicity or less after a 4-week delay in therapy, remove from study.

Ancillary Treatment
  Mild myalgia/arthralgia can be managed with acetaminophen or non-steroidal anti-inflammatory agents.
Toxicity is Monitored and Adverse Reactions Reported
Treatment Evaluation
  Schedule of Evaluations: For the purposes of this study, patients are reevaluated every 6 weeks. In addition to a baseline scan, confirmatory scans are also obtained 6 weeks following initial documentation of objective response.
  Guidelines for Evaluation of Measurable disease
  Minimum disease requirement is 1 cm×1 cm. All measurements are recorded in metric notation using a ruler or calipers. All baseline evaluations are performed as close as possible to the treatment start and not more than 14 days before the beginning of the treatment.
  The same method of assessment and the same technique is used to characterize each identified and reported lesion at baseline and during follow-up. Imaging-based evaluation is preferred to evaluation by clinical examination when both methods have been used to assess the antitumor effect of a treatment.
  Clinical lesions are considered measurable only when they are superficial (e.g. skin nodules, palpable lymph nodes). In the case of skin lesions, documentation by color photography including a ruler to estimate the size of the lesions is recommended.
  Lesions on chest x-ray are acceptable as measurable lesions when they are clearly defined and surrounded by aerated lung. However, CT is preferred.
  Conventional CT and MRI is performed with cuts of 10 mm or less in slice thickness contiguously. A single technique of imaging is employed in all assessments of tumor response throughout the study.

Cytology and Histology:
  If the measurable disease is restricted to a solitary lesion, its neoplastic nature is confirmed by cytology/histology.
  These techniques can be used to differentiate between partial response and complete response in rare cases, for example, residual lesions in tumor types such as germ cell tumors, where known residual benign tumors can remain.
  The cytological confirmation of the neoplastic origin of any effusion that appears or worsens during treatment when the measurable tumor has met criteria for response of stable disease is mandatory to differentiate between response or stable disease (an effusion may be a side effect of the treatment) and progressive disease.

Measurement of Effect
  Target Lesions
    All measurable lesions up to a maximum of 10 lesions representative of all involved organs are identified as target lesions and recorded and measured at baseline. Target lesions are selected on the basis of their size (lesions with the longest diameter) and their suitability for accurate repetitive measurements (either by imaging techniques or clinically).
    The sum of the longest diameter (LD) for all target lesions is calculated and reported as the baseline sum LD. The baseline LD is used as reference to further characterize the objective tumor response of the measurable dimension of the disease.
  Non-Target Lesions: All other lesions (or sites of disease) are identified as non-target lesions and are also recorded at baseline. Measurements are not required, and these lesions are followed as "present" or "absent".

Response Criteria
Evaluation of target lesions
  Complete Response (CR): Disappearance of all target lesions.
  Partial Response (PR): At least a 30% decrease in the sum of the longest diameter (LD) of target lesions taking as reference the baseline sum LD.
  Progression (PD): At least a 20% increase in the sum of LD of target lesions taking as reference the smallest sum LD recorded since the treatment started or the appearance of one or more new lesions.
  Stable Disease (SD): Neither sufficient shrinkage to qualify for PR nor sufficient increase to qualify for PD taking as references the smallest sum LD.
Evaluation of non-target lesions
  Complete Response (CR): Disappearance of all non-target lesions and normalization of tumor marker level.
  Non-Complete Response (non-CR): Persistence of one or more non-target lesions and/or maintenance of tumor marker level above the normal limits.
  Progression (PD): Appearance of one or more new lesions. Unequivocal progression of existing non-target lesions.
  Note: Although a clear progression of "non-target" lesions only is exceptional, in such circumstances, the opinion of the treating physician should prevail, and the progression status should be confirmed at a later time by the review panel (or study chair).
  If tumor markers are initially above the upper normal limit, they must normalize for a patient to be considered in complete clinical response.

Confirmation

To be assigned a status of PR or CR, changes in tumor measurements are confirmed by repeat studies that should be performed 6 weeks after the criteria for response are first met.

In the case of SD, follow-up measurements must have met the SD criteria at least once after study entry at a minimum interval of 6 weeks.

Evaluation of Best Overall Response

The best overall response is the best response recorded from the start of the treatment until disease progression/recurrence (taking as reference for progressive disease the smallest measurements recorded since the treatment started). The patient's best response assignment will depend on the achievement of both measurement and confirmation criteria (see section 11.41).

| Target Lesions | Non-Target Lesions | New Lesions | Overall Response |
|---|---|---|---|
| Complete response | Complete response | No | Complete response |
| Complete response | Non-CR/Non-PD | No | Partial response |
| Partial response | Non-PD | No | Partial response |
| Stable disease | Non-PD | No | Stable disease |
| Progressive disease | Any | Yes or No | Progressive disease |
| Any | Progressive disease | Yes or No | Progressive disease |
| Any | Any | Yes | Progressive disease |

Patients with global deterioration of health status requiring discontinuation of treatment without objective evidence of disease progression at that time are reported as "symptomatic deterioration." Every effort is made to document the objective progression even after discontinuation of treatment.

In some circumstances it may be difficult to distinguish residual disease from normal tissue. When the evaluation of complete response depends upon this determination, it is recommended that the residual lesion be investigated (fine needle aspirate/biopsy) before confirming the complete response status.

Duration of Response

Duration of overall response is measured from the time measurement criteria are met for CR/PR (whichever is first recorded) until the first date that recurrent or progressive disease is objectively documented (taking as reference for progressive disease the smallest measurements recorded since the treatment started).

Duration of overall complete response is measured from the time measurement criteria are first met for CR until the first date that recurrent disease is objectively documented.

Duration of stable disease is measured from the start of the treatment until the criteria for progression are met, taking as reference the smallest measurements recorded since the treatment started.

Descriptive Factor Disease Status: None

Treatment/Follow-up Decision at Evaluation of Patient

Patients in whom disease has not progressed and who have experienced acceptable toxicity are eligible for re-treatment at the same dose level for the duration of the study until 24 weeks. After 25 weeks, continual treatment every 3 months up to 18 months post randomization is at the discretion of the clinician.

Patients in whom disease has not progressed and who have experienced unacceptable toxicity are eligible for re-treatment at a lower dose (see Section 8.0) until week 24 of the study. After 25 weeks, continued treatment every 3 months for up to 18 months post randomization is at the discretion of the clinician. Re-treatment of patients with grade 3 or 4 toxicities, other than those identified in the dose modification table, is discussed with the study chair before receiving further protocol therapy.

Those patients with progression of disease or who refuse further treatment will go to the event-monitoring phase. Tumor progression and death is monitored every 3 months until death or 3 years post randomization. No follow-up is required after 3 years post randomization.

Re-treatment of patients: Decisions regarding re-treatment of any patient is based upon the type, severity, duration, and reversibility of the toxic reactions. In general, patients who show improvement or stability of their disease continues to receive treatment beyond the 24-week duration of the study. Immunizations are performed at 3-month intervals. Patients having objective progression of disease or clinical deterioration will not continue to receive treatment on this study.

If a patient fails to complete the initial cycle of therapy (defined as drug administration and 3 weeks observation) for reasons other than toxicity, the patient is regarded as treatment intolerant and an additional patient is treated at the current dose level; however, all toxicity information will be utilized in the analysis. For these instances, a specific notation is made for review by a study committee.

Pharmacologic/Ancillary Studies

Immunological Assays: The principal objective of monitoring the CTL response to gp-100 is to estimate the effect of in vivo priming with peptides in conjunction with administration of GM-CSF on the frequency of CTLs specific for these peptides. Such estimates can not be accurately derived from standard assays of CTL function, i.e. target lysis, but rather require methods that actually estimate the frequency of CTLs. Two relatively new approaches to estimating CTL frequency are promising for this purpose: (1) staining with class I tetramers and (2) intracellular staining for cytokine production. Class I tetramers are comprised of monomeric class I heavy chains that have been folded with $\beta$2-microglobulin ($\beta$2M) and specific immunogenic peptides; these monomers are then biotinylated at sites on their carboxy ends for conjugation into tetramers with PE-avidin. Such tetramers have increased valency and can be mixed with FITC-labeled anti-CD8 antibody to stain peptide-specific CTLs for enumeration by flow cytometry. Intracellular staining for cytokines provides a complementary approach in which CTLs are boosted in vitro with peptide-sensitized stimulator cells in the presence of Brefeldin A that blocks transport such that cytokines accumulate in the responding cells. Stimulated cells are then permeabilized and stained with anti-cytokine and anti-CD8 antibodies to estimate the frequency of specifically responding $CD8^+$ T cells by flow cytometry. Both approaches can be used to estimate the effect of in vivo peptide priming on the frequency of specific CTLs.

One hundred milliliters of blood is drawn prior to initiation of peptide immunization and at 7 d after each immunization. Peripheral blood lymphocytes (PBLs) are enriched by flotation in Ficoll gradients and frozen in 10% DMSO for storage. PBLs from each blood draw are tested with a panel of monoclonal antibodies to estimate the percentages of $CD4^+$ and $CD8^+$ T cells as well as B cells, monocytes, and dendritic cells.

In addition, assays are performed to estimate T cell responses to polyclonal stimulus (PHA), recall antigens (tetanus toxoid), and HLA alloantigens. These two sets of experiments are used for evaluation of overall T cell responsiveness.

PBLs are stimulated with the melanoma peptide to stimulate and expand CTLs specific for the vaccine gp100 peptide and influenza (GILGFVFTL; SEQ ID NO:20) peptides. Briefly, PBLs are diluted to $2.5 \times 10^6$ cells/ml and incubated at 37° C./5% $CO_2$ in the presence of 100 μg peptide in round bottom microtiter wells. After 3 d of culture, recombinant IL-2 is added to a concentration of 20 U/ml. Responder T cells are harvested after 6-7 d of culture and mixed in a standard cell mediated lympholysis (CML) assay at varying ratios with $^{51}Cr$-labelled target cells sensitized with titrated concentrations of peptide. Target cells include T2 and 221.A2 cells and sensitizing peptides include the specific target peptide as well as a negative control. These assays are used to identify those PBL samples that include CTLs specific for the melanoma peptide and provide a first-order comparison of CTL function.

More definitive estimates of specific CTL frequency are generated through tetramer analysis. The plasmid vectors for synthesis of human β2M and HLA-A2 heavy chains were obtained. The laboratory successfully folded HLA-A2 heavy chain monomers that include melanoma peptides. A2 heavy chain molecules are mixed with b2M and gp100 and influenza peptides. Folded monomers are biotinylated with BirA enzyme and conjugated with PE-avidin. Each tetramer preparation is tested with specific CTLs to confirm activity. The CTL lines were generated by repeated stimulation of PBLs collected from normal HLA-A2+ donors with the specific peptide.

Double staining with PE-labeled tetramers and FITC-labeled anti-CD8 monoclonal antibody are performed in the presence of Fc receptor-specific antibody to block non-specific staining. Stained cells are analyzed by flow cytometry and estimates of the percentages of doubly stained CTLs are obtained. Pre-immunization PBLs are compared with PBLs collected after each of the successive peptide immunizations to assess the efficiency of peptide immunization on CTL frequency. Tetramers are also used to specifically sort CD8+ CTLs for functional assays. Sorting is performed to purify tetramer/CD8 double positive cells that are expanded 10 d with ConA and IL-2; these expanded CTLs are tested with peptide-sensitized targets in a standard CML assay to confirm that the sorted CTLs exhibit lytic function.

Estimates of peptide-specific CTLs are also be obtained by intracellular staining for cytokines following in vitro stimulation with peptide-sensitized stimulator cells. Pre- and post-immunization PBLs are stimulated with individual peptides as outlined above. After 7 d of culture, cells are diluted and stimulated with T2 cells pulsed with peptide for 5-6 hr in the presence of Brefeldin A. Responder cells are then fixed, permeabilized, and stained with anti-CD8 antibody in conjunction with antibodies specific for IFN and GM-CSF for flow cytometric analysis. These assays yield the frequencies of CTLs that are responsive to peptide stimulation through cytokine release.

Estimates of peptide-specific, IFN-gamma-producing CTLs and Th cells are obtained by Elispot assays following in vitro stimulation with peptide-sensitized stimulator cells. CD8+ (CTLs) and CD4+ (Th cells) are purified from pre- and post-immunization PBLs by magnetic bead separation. These responder cells are stimulated with autologous CD8−/CD4− PBLs pulsed with the gp 100 peptide. After 7 d of culture, cells will be diluted, titrated and stimulated with T2 cells pulsed with peptide for 16-24 hr in microtiter wells coated with anti-IFN-gamma capture antibody. The test peptides include the gp100 peptide and a negative control peptide (influenza). The wells are then washed and treated with ALP-conjugated detection antibody for estimation of the number of spots observed for each responder cell titration. The difference between the frequency of spots obtained with gp 100 and influenza peptide stimulation is the estimate of the frequency of gp 100 peptide-specific, IFN-gamma-producing T cells with either the CD8+ or CD4+ phenotype. In parallel, CD8+ and CD4+ T cells are stimulated with T2 cells pulsed with gp100 and influenza peptide and harvested after 6 hr for total RNA extraction. Quantitative, competitive RT-PCR is performed to estimate the numbers of copies of IFN-gamma message/ng total RNA. These three assays are used to evaluate the effects of peptide immunization on (1) the frequency of CTLs that recognize the gp100 peptide, (2) the frequencies of CTLs and Th cells that produce IFN-gamma in response to the gp100 peptide, and (3) the total amount of IFN-gamma message produced by CTLs and Th cells in response to the gp100 peptide.

Delayed-type Hypersensitivity (DTH) Testing: General cell-mediated immunity is functionally assessed by DTH testing prior to the initiation at the conclusion of therapy. A standard antigen series, including *Candida*, mumps and tetanus is applied to the left or right volar forearm of each patient. 0.1 ml of a standard, commercial preparation of each antigen is injected intradermally. Forty-eight hours later, each injection site is visually observed and the extent of erythema and induration recorded on a scale of 0-4. The number of positive test sites is compared before and after therapy. If the patient demonstrates energy (no positive test sites) prior to initiation of therapy, he/she will still be eligible for enrollment.

Patients are also tested to the individual peptide antigens at a dose of 10 μg peptide saline solution. Initial testing is performed prior to initiation of therapy and also prior to cycle 7. Extent of erythema and induration is recorded in an identical manner as the standard antigen battery.

Tuberculin syringes pre-loaded with 10 μg of peptide in 100 μL of IFA are injected intradermally in the extremities/areas of the body away from sites of prior immunizations with the peptide vaccines.

Lymph node aspiration: If there is clinical evidence of lymph node enlargement in the region of immunization, a fine needle aspiration biopsy of the lymph nodes is performed. The collected specimens are studied for frequency of CTLs directed against the peptide vaccine.

Sample Schedule (in weeks): Cycle length is 21 days

| Cycle of Rx | Pre-Rx | 1 | 2 | 3 | 4 | 5 | 6 | 7 | 8 |
|---|---|---|---|---|---|---|---|---|---|
| Week of study | — | 0 | 3 | 6 | 9 | 12 | 15 | 18 | 24 |
| Treatment | | X | X | X | X | X | X | X | X |
| CBC, CHEM | X | | X | X | X | X | X | X | X |
| Immunologic tests | X | | X | X | X | X | X | X | X |
| Injection site reaction | | | X | X | X | X | X | X | X |
| DTH | X | | | | | | | | X |
| Node aspirate[1] | | | | | | | | | X |

[1]Only if node is clinically enlarged.

Sample Preparation: Peripheral blood is collected in purple top Vacutainer tubes. A special study refer card is generated to identify these specimens. The samples are kept at room temperature until use, which will be within 2 hours of collection.

Vaccine Information

Melanoma Peptides

Storage and Stability:

Store intact vials frozen at −10° to −20° C. The Tyrosinase peptide is labeled for refrigerated storage, but can be frozen to allow storage with the other peptides; freezing does not negatively effect the stability of the solution. Thawed vials may be stored for up to 6 hours at refrigerated temperatures. Once thawed, the peptide is used within 3 hours when kept at room temperature. Long-term stability of the peptides in intact vials is under evaluation through an on-going stability testing program.

Montanide ISA 51 Adjuvant (Incomplete Freund's Adjuvant, IFA)

Montanide ISA 51, NSC 675756, is an oil-based adjuvant product similar to Incomplete Freund's Adjuvant which, when mixed with a water-based solution on 1:1 w/w ratio, forms a water-in-oil emulsion. It consists of a highly purified oil, Drakol VR, and a surfactant, mannide oleate. Montanide ISA 51 is manufactured by Seppic, Inc., and is provided in amber glass ampoules containing 3 mL of the solution. Montanide ISA 51 is provided through the Cancer Therapy Evaluation Program, NCI. Montanide ISA 51 is an Investigational New Drug.

Mode of Action:

Acts to enhance immune response to vaccination.

Storage and Stability:

The solution is stored at controlled room temperature. Exposure to cold temperatures may result in a clouded solution, which should be discarded. An expiration date is printed on the ampoule label.

Compatibility Notes:

This solution can be filtered as it's being withdrawn from the glass ampoule to remove any glass particles. The oil will break down the rubber tip of the plunger on syringes; it is advisable to use a different syringe for each ampoule. Do not allow the Montanide ISA 51 to be in direct contact with the rubber tip of the plunger for more time than is necessary to withdraw the solution and inject it into the peptide vial. Fresh syringes can be used to withdraw the emulsified vaccine from the vaccine vial. Once the emulsion is made, there is less interaction of the oil directly with the rubber tip of the plunger.

GM-CSF (Leukine®, sargramostatin)

For this protocol, the lyophillized version of Leukine is used. Each vial contains 250 mcg of sargramostim, 40 mg mannitol, 10 mg sucrose, NF and 1.2 mg tromethamine.

Preparation and Storage:

Aseptically reconstitute a 250 mcg vial with 1.0 mL Bacteriostatic Water for Injection, USP. During reconstitution, the diluent is directed at the side of the vial and the contents gently swirled to avoid foaming. Do not agitate or shake. The reconstituted Leukine solution is clear, colorless, isotonic with a pH of 7.4±0.3, and contains 250 mcg/ml of sargramostim. When reconstituted in this manner, the solution is stable for up to 20 days when stored at 4-8° C. Do not freeze. Unused vials should be stored as per the manufacturer's direction.

Vaccine Preparation Instructions

General Vaccine Preparation Information

Emulsify each peptide or peptide/GM-CSF mixture individually with Montanide ISA-51. Prepare the vials as directed for each group below. Place the vials upside down in a tube platform holder of a vortex machine and vortex at highest speed for 12 minutes. This will minimize the amount of emulsion adhering to the inside surface of the vial. Because neither the peptide solution nor the Montanide ISA-51 contain preservatives or bacteriostatics, the prepared peptide vaccines should be administered as soon as possible.

Group A

Remove the peptide vial from the freezer and allow thawing at room temperature. Once thawed, add 1.2 mL of Montanide ISA to the vial and vortex.

Group B

Remove one vial of the peptide from the freezer and allow thawing at room temperature. Reconstitute a vial of GM-CSF (sargramostatin), 250 mcg, with 1 mL Bacteriostatic Water for Injection, USP, yielding a concentration of 250 mcg/mL. Add 0.25 mL of this solution (62.5 mcg) to the peptide vial. Add 1.25 mL of Montanide ISA 51 to the peptide vial. Load two tuberculin syringes with equal volumes of this solution prior to use. Discard unused GM-CSF.

Group C

Remove one vial of the peptide from the freezer and allow thawing at room temperature. Reconstitute a vial of GM-CSF (sargramostatin), 250 mcg, with 1 mL Bacteriostatic Water for Injection, USP, yielding a concentration of 250 mcg/mL. Add 0.4 mL of this solution (100 mcg) to the peptide vial. Add 1.25 mL of Montanide ISA 51 to the peptide vial. Load two tuberculin syringes with equal volumes of this solution prior to use. Discard unused GM-CSF.

Vaccine Administration Information

Dose Specifics:

Each peptide vaccine will consist of a total volume of 1-1.5 mL containing 1 mg of the peptide, 1 mL of Montanide ISA 51 (1.0 mL) and, for Group B, ~50 µg GM-CSF (1.25 mL), or, for Group C, ~100 µg GM-CSF (1.5 mL).

Administration:

Vaccinations are given on day 0 of each treatment cycle. Due to the large volume, each peptide vaccine is administered in 2 shots in a contiguous location (a total of 2 shots per vaccination session). The peptide vaccines should be injected in the vicinity of one of the major nodal basins. This basin must not have been dissected. Subsequent immunizations should be rotated among available nodal basins (both arms or thighs).

Site and date of administration are recorded in the treatment record.

Nursing Implication:

Inform patient of possible side effects. Answer any questions.

Do not premedicate unless absolutely necessary. Acetaminophen is the preferred analgesic if needed, but nonsteroidal anti-inflammatory agents or aspirin may be used. Diphenhydramine may be used to reduce erythema if needed.

Monitor for acute reactions. Outpatients may need to be observed for 1-2 hours after receiving first dose.

Vaccine Side Effects

Because of the low dose of GM-CSF used and the slow-release nature of the vaccine emulsion, side effects normally seen with systemic treatment doses of GM-CSF should not play a factor in this vaccination treatment. Expected side effects are related to the peptides (vitiligo) and Montanide ISA 51. It is possible that the GM-CSF may potentiate the reaction seen at the injection site.

Dermatology/Skin: Injection site reaction, rare granuloma formation, possible development or worsening of pre-existing vitiligo, rash.

Hepatic: Transient rises in liver transaminases.

Constitutional: Low-grade fever.

Ocular/Visual: Possible damage to the eye (no reported incidences to date).

Statistical Considerations and Methodology:

Study design: This is a pilot study designed to determine the immunological effects of tumor vaccine (differentiation antigen peptide) challenge in the presence of various concentrations of immune adjuvants GM-CSF and incomplete Freund's adjuvant. The secondary goals of the study examine the toxicity profile of each treatment combination and report the number of objective responses observed.

The study design chosen for this proposal is a stratified randomized design with type of dominant disease (see section 5.0) as the sole stratification factor. This design was chosen rather than that of a traditional phase I design as the dose levels of each reagent are quite low (GM-CSF doses are below 10% of commonly used doses). At these levels, the anticipated number of toxicities and their severity are thought to be minimal. Toxicities will be carefully monitored and accrual will be suspended if 2 or more of the first six patients experience a grade 4 hematologic toxicity lasting for 5 or more days or a rise in serum creatinine to levels 2 or more times that of their baseline value.

Accrual: Ten patients with stage 1V malignant melanoma are randomized to each one of the 3 treatment combinations. The total number of eligible patients to be accrued is 30. Patients are allocated to each dose level using a dynamic allocation procedure that balances the marginal distribution of type of dominant disease between treatment combinations.

Endpoints: The primary end points for this pilot study are the changes in tumor antigen peptide specific immune responses (in vitro and DTH) from pretreatment levels. PBLs are tested with a panel of monoclonal antibodies to estimate the percentage of CD4+ T cells, CD8+ T cells, B cells, monocytes, and dendritic cells. Double staining with PE-labeled tetramers and FITC-labeled anti-CD8 monoclonal antibody is performed in the presence of Fc receptor specific antibody and the percentage of double stained CTLs will be obtained.

Forty-eight hours after injection, each injection sight is inspected for the extent of erythema and induration.

Secondary end points include the number and severity of hematologic and non-hematologic toxicities observed and the proportion of objective responses observed. All patients meeting the eligibility criteria who have signed a consent form and who have begun treatment are considered evaluable for the estimation of the objective response proportion. The objective response proportion is estimated by the number of patients with an objective status of complete response or partial response on two consecutive tumor evaluations at least 6 weeks apart divided by the total number of patients evaluable for response.

Analysis plan: No formal hypothesis testing is performed in this study. Agreement between the two methods used to estimate CTL frequency is assessed using the graphical methods proposed by Bland and Altman. The analysis plan for the gp-100 peptide antigen and GM-CSF is as follows: Plots are constructed of the of the percent of CD4+ T cells, CD8+ T cells, B cells, monocytes, dendritic cells and double stained CTLs present against time. Also, plots of the percent change in these factors from their pretreatment levels against time will be constructed. These plots enable visual assessment of patterns of change and variability within a treatment regimen and between treatment regimens. The extent of erythema and induration 48 hours after injection is plotted against time for the peptide antigen and GM-CSF to assess whether extent of erythema and induration is a function of the number of injections or peptide antigen/GM-CSF pair.

Optimal immunization strategies are those which produce a 5 fold increase from pretreatment level 6 in most of these variables, which is maintained at least 6 weeks in 7 out of 10 patients treated at that level, with little toxicity and a small degree of erythema/induration.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified polypeptide comprising an HTL epitope and the amino acid sequence as set forth in SEQ ID NO:17, wherein said polypeptide is 13 to 30 amino acids long.

2. The polypeptide of claim 1, wherein said polypeptide comprises the amino acid sequence as set forth in SEQ ID NO:6.

3. The polypeptide of claim 1, wherein said polypeptide binds more than one MHC class II allele.

4. The polypeptide of claim 1, wherein said polypeptide binds HLA-DR-53 or HLA-DQw6.

* * * * *

UNITED STATES PATENT AND TRADEMARK OFFICE
CERTIFICATE OF CORRECTION

PATENT NO.       : 7,795,381 B2
APPLICATION NO.  : 12/018022
DATED            : September 14, 2010
INVENTOR(S)      : Esteban Celis It is certified that error appears in the above-identified patent and that said Letters Patent is hereby corrected as shown below:

Title Page, References Cited, Other Publications, Fritsch et al. reference, please delete "lmmunohistologic" and insert --Immunohistologic-- therefor.

Signed and Sealed this
Second Day of August, 2011

David J. Kappos
*Director of the United States Patent and Trademark Office*